US012586674B1

(12) United States Patent　　　　　(10) Patent No.:　US 12,586,674 B1
Mukhopadhyay　　　　　　　　　　　(45) Date of Patent:　　Mar. 24, 2026

(54) CHRONIC PAIN AND FOOD TRIGGER TRACKING SYSTEM AND PROCESSES

(71) Applicant: Anosua Mukhopadhyay, San Jose, CA (US)

(72) Inventor: Anosua Mukhopadhyay, San Jose, CA (US)

( * ) Notice: Subject to any disclaimer, the term of this patent is extended or adjusted under 35 U.S.C. 154(b) by 0 days.

(21) Appl. No.: 18/769,310

(22) Filed: Jul. 10, 2024

Related U.S. Application Data

(60) Provisional application No. 63/525,880, filed on Jul. 10, 2023.

(51) Int. Cl.
　　*G16H 20/60*　　(2018.01)
　　*G16H 10/20*　　(2018.01)
　　*G16H 10/60*　　(2018.01)
　　*G16H 15/00*　　(2018.01)
　　*G16H 50/30*　　(2018.01)
　　*G16H 50/70*　　(2018.01)
　　*G16H 80/00*　　(2018.01)
　　*G01N 33/48*　　(2006.01)
(52) U.S. Cl.
　　CPC ............. *G16H 20/60* (2018.01); *G16H 10/60* (2018.01); *G16H 50/70* (2018.01); *G16H 10/20* (2018.01); *G16H 15/00* (2018.01); *G16H 50/30* (2018.01); *G16H 80/00* (2018.01)
(58) Field of Classification Search
None
See application file for complete search history.

(56) References Cited

U.S. PATENT DOCUMENTS

2017/0148349 A1*　5/2017　Speigel et al.
2019/0304581 A1*　10/2019　Leppard et al.

OTHER PUBLICATIONS

Judge 2019. Symptom and Food Tracking Apps for IBS. "https://gutivate.com/blog/apps" (Year: 2019).*
Bimuno 2022. Top 5 apps for IBS and digestive health "https://www.bimuno.com/news/gut-health/top-5-apps-for-ibs-digestive-health/?srsltid=AfmBOoqvM-iq8bslqJXCpsBWKqXfOafVz2TrUDDR7_vMi8BMzOOtuCV7" (Year: 2022).*
Clevers, Egbert et al. "Relations between Food Intake, Psychological Distress, and Gastrointestinal Symptoms: A Diary Study." United European Gastroenterology journal 7.7 (2019): 965-973. Web. (Year: 2019).*
TodaysNewIdea. Have a food tolerance out app can help "https://todaysnewidea.co.uk/content/product/fit/" Posted Dec. 1, 2021 (Year: 2021).*

(Continued)

*Primary Examiner* — Karlheinz R. Skowronek
*Assistant Examiner* — Joseph Pulliam

(57)　　　　　ABSTRACT
A machine-learning based, interactive chronic pain and food trigger tracking system and processes and a cross-platform chronic pain and food trigger tracking app are disclosed. A machine learning algorithm automatically categorizes pain symptoms against food input and categorizes the input in taxonomic categories to give users feedback on whether a food could be contributing to their pain intensity. Dialectic behavior therapy guides users through chronic pain management. The machine-learning based, interactive chronic pain and food trigger tracking system also determines possibilities of supplements helping, hurting, or not having an effect on pain intensity.

17 Claims, 9 Drawing Sheets

(56)     References Cited

OTHER PUBLICATIONS

Alves, Tatiane Vieira, et al. "Interactive Protocol for Acquisition of Migraine Diaries with a Mobile App and Machine Learning Data Analysis." Proceedings of the XX Brazilian Symposium on Human Factors in Computing Systems. New York, NY, USA: ACM, 2021. 1-9. Web. (Year: 2021).*

Back 2012 "Back-end development of mobile application for the collection of dietary data" (Year: 2012).*

Goldstein, Pavel et al. "Emerging Clinical Technology: Application of Machine Learning to Chronic Pain Assessments Based on Emotional Body Maps." Neurotherapeutics 17.3 (2020): 774-783. Web. (Year: 2020).*

Limketkai, Berkeley N et al. "The Age of Artificial Intelligence: Use of Digital Technology in Clinical Nutrition." Current surgery reports (Philadelphia, PA) 9.7 (2021): n. pag. Web. (Year: 2021).*

* cited by examiner

700

CHRONIC PAIN AND FOOD TRIGGER TRACKING SYSTEM AND PROCESSES

CLAIM OF BENEFIT TO PRIOR APPLICATION

This application claims benefit to U.S. Provisional Patent Application 63/525,880, entitled "A MACHINE LEARN-ING-BASED INTERACTIVE DIALECTICAL BEHAV-IOR THERAPY-ORIENTED CHRONIC HEALTH CON-DITION MONITORING PROCESS FOR TRACKING OMEGA TYPE NUTRIENTS, PROBIOTIC SUPPLE-MENTS, AND REACTIONS THAT MAY OCCUR IN CONNECTION WITH CHRONIC HEALTH CONDI-TIONS," filed Jul. 10, 2023. The U.S. Provisional Patent Application 63/525,880 is incorporated herein by reference.

BACKGROUND

Embodiments of the invention described in this specifi-cation relate generally to food/nutrient tracking, food sen-sitivity monitoring, and chronic health condition applica-tions, and more particularly, to a machine-learning based, interactive chronic pain and food trigger tracking system and associated chronic pain and food trigger tracking processes.

Many people experience chronic pain with unknown causes and unknown cures. They may wonder if a certain food, supplement, nutrient, etc., could be contributing to their pain. Some people go on an elimination diet in an attempt to find food culprits.

Additionally, people suffering from chronic pain are often told that probiotics or certain supplements could help alle-viate or eliminate their pain. However, there is no methodi-cal way to determine whether such probiotics or supple-ments have an impact on a person's pain or not.

Also, there is no existing systems, devices, or other mechanisms that utilize even basic statistics to correlate food tracking and chronic pain symptoms. There are some existing apps that determine possible allergens from nutri-tional information, but the possible allergens are not com-plete and such apps do not link suspect allergens to chronic pain experienced by users.

Therefore, what is needed is a way for users to track their food intake in connection with pain symptoms to identify foods that trigger pain or change pain intensity.

BRIEF DESCRIPTION

A machine-learning based, interactive chronic pain and food trigger tracking system and chronic pain and food trigger tracking processes are disclosed. In some embodi-ments, the machine-learning based, interactive chronic pain and food trigger tracking system is configured to track a user's intake of food and identify reactions in connection with chronic pain and health conditions. In some embodi-ments, the machine-learning based, interactive chronic pain and food trigger tracking system is a cloud-based system comprising a front-end web server and a backend chronic pain and food trigger tracking server that hosts a chronic pain and food trigger tracking cloud application service. In some embodiments, the chronic pain and food trigger track-ing cloud application service is accessible to users through a chronic pain and food trigger tracking software application (or "app"). In some embodiments, the chronic pain and food trigger tracking software application comprises a chronic pain and food trigger tracking mobile app. In some embodi-ments, the chronic pain and food trigger tracking software application comprises a chronic pain and food trigger track-ing web app.

In some embodiments, the chronic pain and food trigger tracking app enables users to enter their food intake and pain symptoms over time. In some embodiments, the chronic pain and food trigger tracking app tracks the food and pain as entered and evaluates whether food is triggering new pain or changes in pain symptoms. Based on the evaluation, the chronic pain and food trigger tracking app provides users with feedback on whether food is triggering new pain or changes in pain symptoms and, when food is a trigger, what food items are specifically implicated in triggering new pain or a change in pain symptoms.

In some embodiments, the machine-learning based, inter-active chronic pain and food trigger tracking system and chronic pain and food trigger tracking processes utilize artificial intelligence (AI)-based algorithms and machine learning trained models to provide users with self-guided insight into their chronic pain and/or chronic health condi-tions. In some embodiments, the AI-based algorithms and machine learning models provide the self-guided insights to users through an interactive, dialectic behavior therapy (DBT)-based approach. In some embodiments, the machine-learning based, interactive chronic pain and food trigger tracking system and chronic pain and food trigger tracking processes provide AI-based predictions based on the AI algorithms and machine learning models that are trained on an initial dataset and routinely retrained by a deep learning algorithm to continuously improve its ability to identify food intake that triggers new pain or change in pain systems, such as experienced by increased inflammation and chronic health issue flare-ups. In some embodiments, the AI-based algorithms comprise one or more deep learning algorithms. In some embodiments, the machine learning trained models are deep learning models that are trained and retrained by a deep learning training unit of the machine-learning based, interactive chronic pain and food trigger tracking system.

In some embodiments, the chronic pain and food trigger tracking processes comprise (i) a meal entry and food identification and storage process for entering meal infor-mation, obtaining food information related to the meal information, and storing the meal and food information in a persistent storage, (ii) a pain symptom entry and tracking process for providing a body location, an intensity, and a type of bodily pain and storing the body location, intensity, and type of pain in a chronic pain database, (iii) a time-monitored chronic pain and food trigger identification machine learning process, and (iv) a time-monitored pain intensity and trigger delta value identification machine learning process for identifying a trigger delta value express-ing a rate of change in pain intensity for a consumption rate of food with a food classification.

The preceding Summary is intended to serve as a brief introduction to some embodiments of the invention. It is not meant to be an introduction or overview of all inventive subject matter disclosed in this specification. The Detailed Description that follows and the Drawings that are referred to in the Detailed Description will further describe the embodiments described in the Summary as well as other embodiments. Accordingly, to understand all the embodi-ments described by this document, a full review of the Summary, Detailed Description, and Drawings is needed. Moreover, the claimed subject matters are not to be limited by the illustrative details in the Summary, Detailed Descrip-tion, and Drawings, but rather are to be defined by the appended claims, because the claimed subject matter can be embodied in other specific forms without departing from the spirit of the subject matter.

BRIEF DESCRIPTION OF THE DRAWINGS

Having described the invention in general terms, reference is now made to the accompanying drawings, which are not necessarily drawn to scale, and wherein.

DETAILED DESCRIPTION

Figure 1:
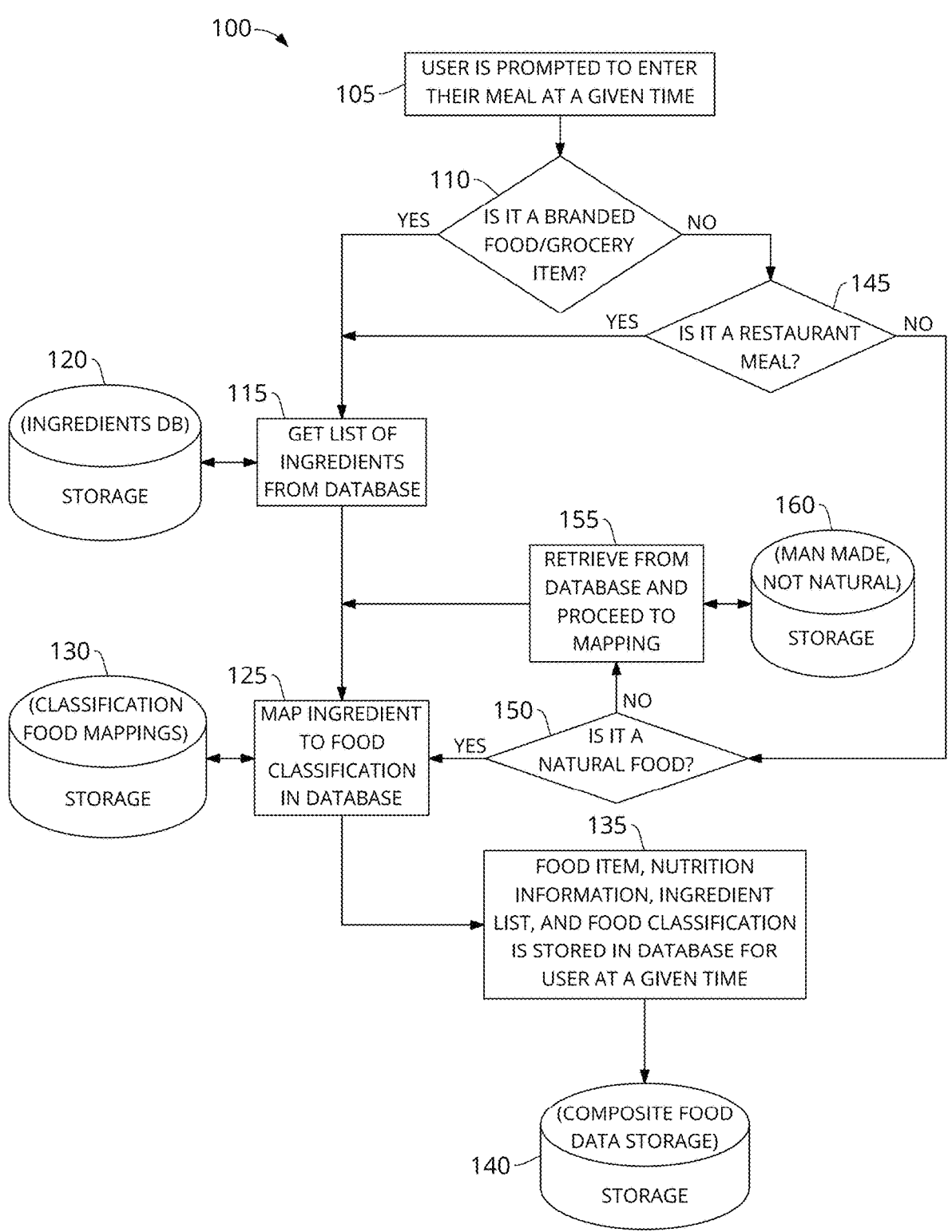
FIG. 1 conceptually illustrates a meal entry and food identification and storage process for entering meal information, obtaining food information related to the meal information, and storing the meal and food information in a persistent storage in some embodiments.

In the following detailed description of the invention, numerous details, examples, and embodiments of the invention are described. However, it will be clear and apparent to one skilled in the art that the invention is not limited to the embodiments set forth and that the invention can be adapted for any of several applications.

Embodiments of the invention described in this specification include a machine-learning based, interactive chronic pain and food trigger tracking system and chronic pain and food trigger tracking processes. In some embodiments, the machine-learning based, interactive chronic pain and food trigger tracking system is configured to track a user's intake of food, food nutrients (both macro-nutrients and micro-nutrients, including different types of omega nutrients), supplements (including probiotic supplements), and food ingredients (hereinafter referred to collectively as "food," "foods," "food items," and/or "food intake") and identify reactions in connection with chronic pain and health conditions. In some embodiments, the machine-learning based, interactive chronic pain and food trigger tracking system is a cloud-based system comprising a front-end web server (with web and mobile app gateways) and a backend chronic pain and food trigger tracking server that hosts a chronic pain and food trigger tracking cloud application service. In some embodiments, the chronic pain and food trigger tracking cloud application service is accessible to users through a chronic pain and food trigger tracking software application (or "app"). In some embodiments, the chronic pain and food trigger tracking software application comprises a chronic pain and food trigger tracking mobile app. In some embodiments, the chronic pain and food trigger tracking software application comprises a chronic pain and food trigger tracking web app.

In some embodiments, the chronic pain and food trigger tracking app enables users to enter their food intake and pain symptoms over time. In some embodiments, the chronic pain and food trigger tracking app tracks the food and pain as entered and evaluates whether food is triggering new pain or changes in pain symptoms. Based on the evaluation, the chronic pain and food trigger tracking app provides users with feedback on whether food is triggering new pain or changes in pain symptoms and, when food is a trigger, what food items are specifically implicated in triggering new pain or a change in pain symptoms.

In some embodiments, the machine-learning based, interactive chronic pain and food trigger tracking system and chronic pain and food trigger tracking processes utilized artificial intelligence (AI)-based algorithms and machine learning trained models to provide users with self-guided insight into their chronic pain and/or chronic health conditions. In some embodiments, the AI-based algorithms and machine learning models provide the self-guided insights to users through an interactive, dialectic behavior therapy (DBT)-based approach. In some embodiments, the machine-learning based, interactive chronic pain and food trigger tracking system and chronic pain and food trigger tracking processes provide AI-based predictions based on the AI algorithms and machine learning models that are trained on an initial dataset and routinely retrained by a deep learning algorithm to continuously improve its ability to identify food intake that triggers new pain or change in pain systems, such as experienced by increased inflammation and chronic health issue flare-ups. In some embodiments, the AI-based algorithms comprise one or more deep learning algorithms. In some embodiments, the machine learning trained models are deep learning models that are trained and retrained by a deep learning training unit of the machine-learning based, interactive chronic pain and food trigger tracking system.

In some embodiments, the chronic pain and food trigger tracking processes comprise (i) a meal entry and food identification and storage process for entering meal information, obtaining food information related to the meal information, and storing the meal and food information in a persistent storage, (ii) a pain symptom entry and tracking process for providing a body location, an intensity, and a type of bodily pain and storing the body location, intensity, and type of pain in a chronic pain database, (iii) a time-monitored chronic pain and food trigger identification machine learning process, and (iv) a time-monitored pain intensity and trigger delta value identification machine learning process for identifying a trigger delta value expressing a rate of change in pain intensity for a consumption rate of food with a food classification.

In some embodiments, the machine-learning based, interactive chronic pain and food trigger tracking system stores ingredients in an ingredients database persistent storage that is accessible for the meal entry and food identification and storage process to retrieve the ingredients of a given meal. In some embodiments, the machine-learning based, interactive chronic pain and food trigger tracking system stores a mapping between a food classification and ingredients in a classification food mapping database persistent storage that is accessible for to the meal entry and food identification and storage process to map the ingredients of a given meal to a food classification in the database. In some embodiments, the machine-learning based, interactive chronic pain and food trigger tracking system comprises a composite food information database persistent storage that incorporates both the ingredients database and the classification food mapping database and stores composite food information (including food item, classification and mapping, nutrition information, ingredients, man-made food information, etc.). An example of a composite food information database persistent storage is described below, by reference to FIG. 5.

In some embodiments, the pain symptom entry and tracking process for providing a body location, an intensity, and a type of bodily pain and storing the body location, intensity, and type of pain in a chronic pain database involves interaction by a user to select a body location of the pain, select a level of pain intensity, and select a type of pain. In some embodiments, the pain symptom entry and tracking process also prompts the user to indicate whether the pain is new pain or is from a known injury and/or a known trigger.

In some embodiments, the time-monitored chronic pain and food trigger identification machine learning process is configured to identify changes in pain over time (pain deltas) and continuously retrain the machine learning model based on the pain deltas and the most recent food and pain entries.

In some embodiments, the time-monitored pain intensity and trigger delta value identification machine learning process is configured to identify a trigger delta value expressing a rate of change in pain intensity for a consumption rate of food with a food classification.

Embodiments of the machine-learning based, interactive chronic pain and food trigger tracking system and chronic pain and food trigger tracking processes described in this specification solve the problems noted above by way of a machine learning model that is trained to identify food in taxonomical categories and to determine if a certain tracked food has several taxonomical categories put into them and are a composite of different food ingredients, etc., so that users need not guess whether there is a particular food present that triggers an increase in pain (or reduces pain in a positive impact). Through the chronic pain and food trigger tracking app, users will be able to sort triggers into lists with the app automatically providing any insights, suggestions, advice, etc. Furthermore, database(s) and/or persistent data storage(s) are accessible through a backend processing system that is configured to automatically categorize common foods, grocery items, and restaurant meals into taxonomical categories. Thus, when a user inputs a food, the backend system is invoked and a search of the database occurs or an update is made as needed. In addition to entering food and meal information, the user is also prompted to enter pain symptoms, selecting the pain location on the user's body (via a 3D body model), the type of pain being experienced, and the intensity of the pain. This entry of pain is not a one-off prompt, but instead, the user may enter as many pain symptoms as they are experiencing or have experienced in terms of their chronic pain symptoms. A machine learning model uses all this data to give feedback to the user on the possibility of whether or not foods from certain taxonomic categories are making their pain symptoms worse. A similar machine learning algorithm is used for a user's supplement usage.

The machine-learning based, interactive chronic pain and food trigger tracking system and chronic pain and food trigger tracking processes of the present disclosure may be comprised of the following elements, components, or steps. This list of possible constituent elements, components, or steps is intended to be exemplary only and it is not intended that this list be used to limit the machine-learning based, interactive chronic pain and food trigger tracking system and chronic pain and food trigger tracking processes of the present application to just these elements, components, and/or steps. Persons having ordinary skill in the art relevant to the present disclosure may understand there to be equivalent elements, components, or steps that may be substituted within the present disclosure without changing the essential function or operation of the machine-learning based, interactive chronic pain and food trigger tracking system and chronic pain and food trigger tracking processes.

1. Users enter food intake for tracking by data entry, capturing images of their food, and/or selection of food items from data resources like databases, etc. Users also track supplements and other alternative health digestible items.

2. Users enter pain symptoms by picking location of pain on an interactive, three-dimensional (3D) model of a human body according to their biological sex. Based on the location of pain, the user is prompted to select or input a type of pain being experienced. In some embodiments, the chronic pain and food trigger tracking app provides a slide tool user interface element that is configured to slide along a track that approximates a range of pain intensity (or sale of pain intensity).

3. Users are able to enter and track multiple symptoms for any given time. A custom user 3D pain model is persistently stored with user-provided pain locations and associated information (intensity of pain, type of pain). Whenever the custom user 3D pain model is updated by user interaction (such as when new pain or changes in pain are experienced), the updates to the custom user 3D pain model are also persistently stored. In some embodiments, time-specific custom user 3D pain models are stored for each time the user inputs pain symptoms (whether new or changes in pain). In this way, a history of chronic pain can be played-back in a view of the custom user 3D pain model that shows a timeline bar and visually outputs pain locations on the body, relative pain intensities, and types of pain in different visual symbols, different colors, or other visual manners.

4. Background (or backend) processing is performed by the machine-learning based, interactive chronic pain and food trigger tracking system. In the background, databases are present for storage of data, such as a database categorizing the food into taxonomies, a database for meal and food information provided by the user, and other databases. In addition to macronutrients and micronutrients being stored like most other food tracking apps, the user's consumed taxonomical categories is also stored.

5. Background processing is continuously performed to determine correlations between a user's food and pain symptoms (e.g., a background batch job, a background continuous process, etc.). Time is another factor that is considered for determining whether there are any significant correlations between food and pain for the user. In some embodiments, probable taxonomical categories are determined when a flare-up of pain is detected. In some embodiments, a probability is calculated for each probable taxonomical category.

6. Users receive a report and notification in user-friendly terms if a certain food seems to be contributing to their pain symptoms. Users may also receive suggested DBT skills to practice over time, or other articles and notifications over chronic conditions, resources to outside communities, etc.

The machine-learning based, interactive chronic pain and food trigger tracking system and chronic pain and food trigger tracking app work by giving users the option to input pain in a user interface of the app that is easy and user-friendly, yet methodical covers all aspects pertinent to the pain being experienced presently or chronic pain symptoms that flare-up and subside over time, but which never seem to go away for good. The app also lets users track their diet (food intake) the way they normally do in other food tracking apps, but code has been developed to automatically determine the taxonomical categories of the user-provided food entries. By capturing pain symptoms and diet/food in identifying their taxonomical categories, a machine learning model can be properly developed with food as the input and pain symptoms as the predicted output. In this case, a classification semi-supervised learning model is used, however as the user gives feedback on if eliminating a certain food helped them, the model becomes more advanced for a user and uses reinforcement learning. Once there are sufficient users, a self-supervised (unsupervised) learning model may be used, while ensuring user privacy.

The machine-learning based, interactive chronic pain and food trigger tracking system and chronic pain and food trigger tracking app also implement and utilize many aspects of DBT to help users stay engaged in the chronic pain and food trigger tracking app to manage their chronic pain. If a user does not have enough of a baseline, then a flare-up cannot be determined, but the user can still use the DBT aspects of the chronic pain and food trigger tracking app to manage pain without a baseline is established.

Once a baseline is established, the machine-learning based, interactive chronic pain and food trigger tracking system and the chronic pain and food trigger tracking app are configured to determine the time between the start of a flare-up and when the triggering food was digested. For example, if the machine-learning based, interactive chronic pain and food trigger tracking system determines that there is a high probability of the user having a sensitivity to gluten, then the machine-learning based, interactive chronic pain and food trigger tracking system and chronic pain and food trigger tracking app will determine the time between when gluten was first digested and the time of the onset of the flare-up.

To make the machine-learning based, interactive chronic pain and food trigger tracking system and chronic pain and food trigger tracking app of the present disclosure, a person may start by creating body models to accept pain input. The body models are preferably 3D interactive models that are configured for user interaction to zoom in and out of body locations, turn the body model around to reveal sides, back and front, etc. However, the body models may be 2D models with views of the front, back, and sides of a body. The body models, whether 3D or 2D, take into account biological sex differences but also factor in the user's preferred gender identity. The chronic pain and food trigger tracking app would need to be coded so that a user interface provide selectable tools, menus, and other options that give users interactive ways to indicate types of pain based on location of the pain on the body model and then let users indicate a relative pain intensity (e.g., on a scale from 0-10, accessible by a slider tool). Then a database needs to store the pain locations, the pain intensities, and the pain types over time. At the same time, the chronic pain and food trigger tracking app would be coded to provide an interface for user entry of meals and food intake, thereby enabling users to track their meals, taking nutrition information for natural foods from the United States Food and Drug Administration (FDA) as well as grocery items (food products) and restaurant foods. The nutrition information would be based on underlying code that is able to parse ingredients automatically and then put them into taxonomical categories or retrieve from an external food product and restaurant food item site. This enables the chronic pain and food trigger tracking app to also store user food/diet information in the database and store the food/diet data in a way that is classified into taxonomical categories over time.

The taxonomical categories and pain model inputs are stored for each particular user over time and are used to run the machine learning models on them to give the user feedback on possible food triggers for their chronic pain. As more users get added, the machine-learning based, interactive chronic pain and food trigger tracking system and chronic pain and food trigger tracking app result in fine-tuning of the machine learning models, which are constantly being retrained. With a large enough user pooling, a more generic unsupervised machine learning model could be used that gives users feedback even earlier on in the process. This is the goal while again ensuring strict user privacy over each user's personal health data.

The databases can be any type, such as relational, object-oriented, flat file, look up table (LUT), etc., but generally need to be capable of scaling in size. In some embodiments, a single database stores all of the data. In some other embodiments, separate databases are used to store food entries of users and meals from restaurants, images of food items ingested by users or labels, such as ingredients shown along a food profile label, etc. This ensures that the machine-learning based, interactive chronic pain and food trigger tracking system and chronic pain and food trigger tracking app is able to analyze ingredient lists from such food profile labels and/or from nutritional information which restaurants may publish to best estimate nutrients from those meals. There needs to be a classification score for each type of nutrient as exact milligrams cannot always be deduced. The database also needs to have tables for supplements, herbs, and minerals. Supplements include commonality in foods, so the database in a preferred embodiment is set up as a relational database to take this into account. However, the input analysis for food versus supplements is different. When a user takes a picture of a supplement versus a food-packaged label, the underlying analysis of how that image is processed differs in the way it determines what is the subject of the image. In some embodiments, image input analysis is performed by an AI computer vision module/algorithm. In some other embodiments, image input analysis is performed by using optical character recognition (OCR). In some embodiments, image input analysis is performed by an AI computer vision module/algorithm.

Also, different machine learning models for supplements and food take into account the tags that work for them and may still rely on the same database used for a user's statistical correlation analysis of possible triggers for health conditions. One may also implement a machine learning model to improve the database over time as users input more data. This database (or databases), growing in scale over time, could actually be open-source and made for public use and healthcare over time. The database of user information, however, needs to be absolutely private, honoring HIPAA and GDPR.

Users who go to a doctor and are told to follow an elimination diet to find out what food items could be causing their symptoms (like IBS or chronic migraines) may now utilize the machine-learning based, interactive chronic pain and food trigger tracking system and chronic pain and food trigger tracking app of the present disclosure to identify food items causing flare-ups of pain and can even use the machine-learning based, interactive chronic pain and food trigger tracking system and chronic pain and food trigger tracking app to better track their elimination diets. In the past, people have done this by pen/paper, rudimentary apps, and always having to guess at the first thing they eliminate. However, these mechanisms failed to evaluate correspondence between food ingestion over time and physical manifestations of pain symptoms. In addition, doctors, health care workers, and other medical personnel could use the machine-learning based, interactive chronic pain and food trigger tracking system and chronic pain and food trigger tracking app as a preventative strategy to detect successful or unsuccessful management of pain for patients and their symptoms.

By way of example, FIG. 1 conceptually illustrates a meal entry and food identification and storage process 100 for entering meal information, obtaining food information related to the meal information, and storing the meal and food information in a persistent storage in some embodiments. The meal entry and food identification and storage process 100 is performed by the chronic pain and food trigger tracking app when a user is operating a device configured to run the chronic pain and food trigger tracking app. The device operated by the user may be a mobile device running either a mobile app version of the chronic pain and food trigger tracking app or a web app version of the chronic pain and food trigger tracking app. Alternatively, the device operated by the user may be a conventional computing device (such as a PC, a laptop, etc.) running the web app version of the chronic pain and food trigger tracking app.

In some embodiments, the meal entry and food identification and storage process 100 starts by prompting the user to enter a meal at a given time (at 105). Note that the user may have been running chronic pain and food trigger tracking app for other aspects before entering meal information. For instance, the user may be interacting with the chronic pain and food trigger tracking app for pain management guidance or DBT therapeutic guidance and only later select an option in the chronic pain and food trigger tracking app to enter a meal (such as by selection of a UI tool, interaction with a data entry field, selection from a menu, etc.). Also, the chronic pain and food trigger tracking app tracks food intake over time, so entering a time at which the user is consuming or has consumed the meal allows for tracking and analysis that is more accurate than meal entry without time input. While it is possible to retrieve time information from the user's device at the time of meal entry, this could inadvertently lead to inaccuracies since a user may not enter their meals right at the moment of consuming those meals. Furthermore, the user is prompted to enter the meal information with specific details, such the brand and type of food, a name of a grocery item that is typically found in grocery stores (e.g., head of lettuce, apple, etc.). The user is also prompted to add any add-on food items that complete the meal (e.g., condiments like ketchup, mustard, salt, spices, etc.). The user may alternatively capture an image, using their mobile device, of a food profile label, which shows the type and brand of food, or shows the grocery item being entered. In some embodiments, the user selects an image and description of a meal from a pre-sorted list of common food items that many people eat as meals. In some embodiments, the pre-sorted list of common food items gets refined over time as the user's common meal habits become more apparent.

Upon entering the meal and time information, the meal entry and food identification and storage process 100 determines whether the meal is a branded food item or grocery item (at 110). When the meal is not a branded food item or grocery item ('NO'), the meal entry and food identification and storage process 100 transitions to a step for determining (at 145) whether the meal is a restaurant meal. When the meal is affirmatively a restaurant meal ('YES'), the meal entry and food identification and storage process 100 moves forward to retrieve ingredients for the meal (at 115), which is described in detail further below. On the other hand, when the meal is not determined (at 145) to be a restaurant meal ('NO'), then the meal entry and food identification and storage process 100 transitions to a step for determining whether the meal is a natural food or not (at 150), which is described further below.

Turning back to the determination (at 110), when the meal is affirmatively expressed to be a branded food or grocery item ('YES'), then the meal entry and food identification and storage process 100 retrieves a list of ingredients (at 115) from an ingredients database (at 120). As noted above, the machine-learning based, interactive chronic pain and food trigger tracking system of some embodiments stores ingredients in an ingredients database persistent storage (which may be, for example, part of a cloud-based composite food information database accessible to the chronic pain and food trigger tracking app by connection to the chronic pain and food trigger tracking cloud application service). The ingredients retrieved from the ingredients database (at 120) for a pre-packaged hamburger of a particular brand or a deli hamburger prepared by a particular grocery deli department may include ½ pound of ground beef and two sourdough buns. Similarly, the meal entry and food identification and storage process 100 retrieves a list of restaurant meal ingredients (at 115) when the meal entered by the user is a restaurant meal. That is, the ingredients database (at 120) may store ingredients for known restaurant meals, menu items, etc., for known restaurants. Notably, in some embodiments, the ingredients database (at 120) may not include all information for each restaurant or grocery food item, as these are continuously updated at many food provider establishments. Thus, in some embodiments, the list of ingredients for the meal may be retrieved from an external site or service (e.g., from the FDA or other site). An example of external sites and services from which meal information may be retrieved is described further below, by reference to FIG. 5.

After retrieving the list of ingredients (at 115) from the ingredients database (at 120), the meal entry and food identification and storage process 100 proceeds to map the ingredients (at 125) to a food classification in the classification food mapping database (at 130). As mentioned above, the machine-learning based, interactive chronic pain and food trigger tracking system of some embodiments stores mappings between food classifications and ingredients in a classification food mapping database persistent storage (which may be, for example, part of a cloud-based composite food information database accessible to the chronic pain and food trigger tracking app by connection to the chronic pain and food trigger tracking cloud application service).

After mapping the ingredients (at 125) of the meal to a food classification as identified in the classification food mappings database (at 130), the meal entry and food identification and storage process 100 stores (at 135) a composite food record in a composite food database persistent storage (at 140). The composite food record comprises an aggregation of all the meal and time related information entered by the user, retrieved from databases, and mapped by the meal entry and food identification and storage process 100. Specifically, the composite food record stored (at 135) in the composite food database (at 140) includes the meal/food item, nutrition information, the list of ingredients, and the food classification in a composite food record along with the time of consumption information provided by the user.

Turning back to the determination (at 150) of whether the meal is a natural food, the meal entry and food identification and storage process 100 has already determined that the meal entered by the user is not a branded food, a grocery item, or a restaurant meal. This means the meal can be a synthetic (man-made) meal or a meal of natural items, such as food from a garden tended by the user, eggs laid by hens at a farm and gathered by the user, mushrooms foraged from a forest by the user, fish caught by the user, etc. When the meal is affirmatively determined (at 150) to be a natural food ('YES'), the meal entry and food identification and storage process 100 proceeds to the step for mapping the ingredients to a food classification (at 125) identified in the classification food mappings database (at 130). On the other hand, when the meal is not a natural food ('NO'), the meal entry and food identification and storage process 100 retrieves information about a man made (synthetic, not natural) food for the meal (at 155) from a man made food database (at 160). Then the meal entry and food identification and storage process 100 proceeds forward to map the ingredients to food classification (at 125) in the classification food mappings database (at 130), followed by aggregating the meal/food item, time of consumption, nutrition information, the list of ingredients, and the food classification into a composite food record and storing the composite food record (at 135) in the composite food database persistent storage (at 140). In this way, the user is able to track all food intake, time of food consumption, and flesh out all foods automatically by the meal entry and food identification and storage process 100 retrieving ingredients and mapping the ingredients to food classifications for tracking in connection with chronic pain symptoms. An example of a user interacting with the chronic pain and food trigger tracking app for pain symptom entry is described next, by reference to FIG. 2.

Figure 2:
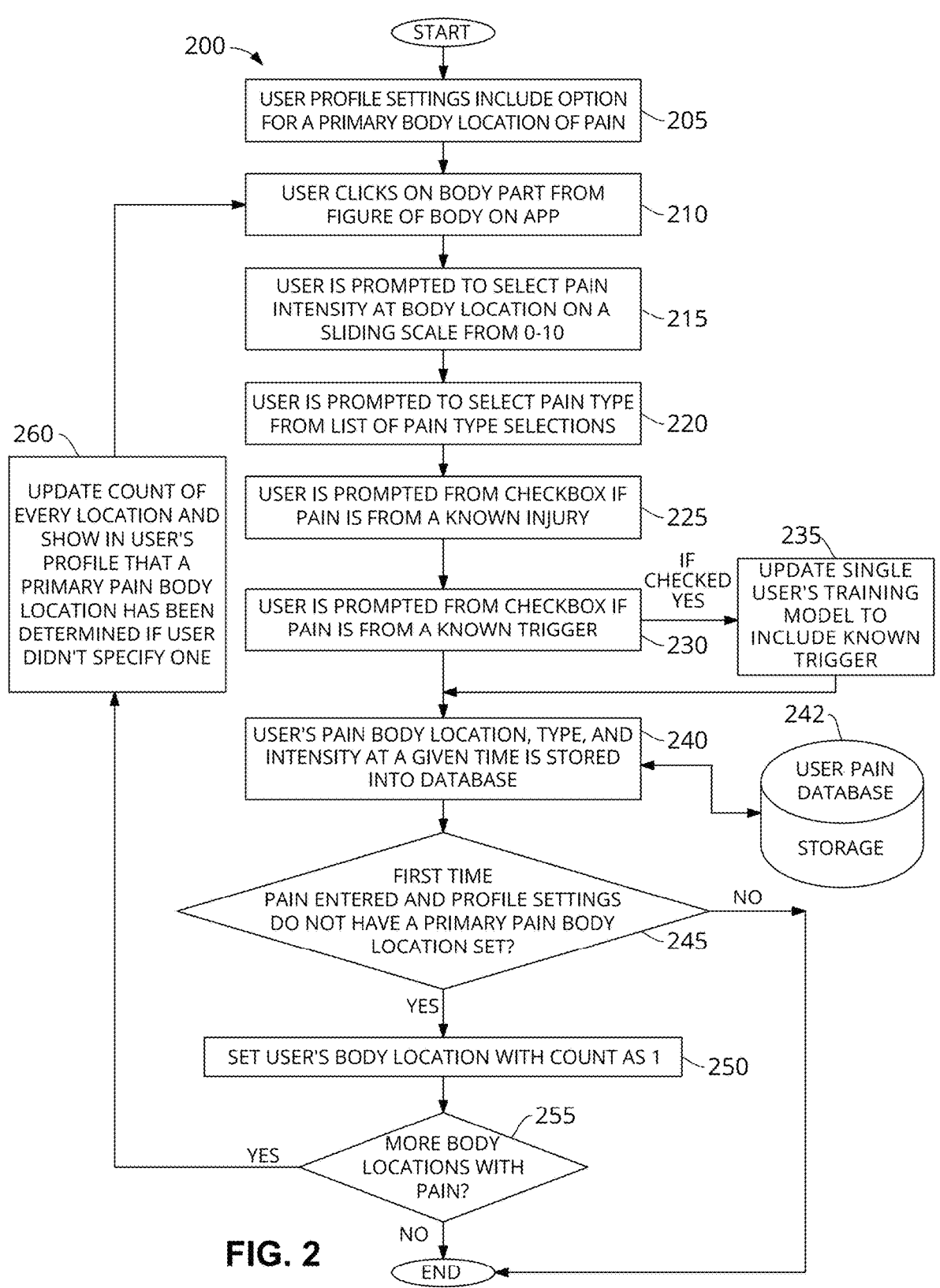
FIG. 2 conceptually illustrates a pain symptom entry and tracking process for providing a body location, an intensity, and a type of bodily pain and storing the body location, intensity, and type of pain in a chronic pain database in some embodiments.

Specifically, FIG. 2 conceptually illustrates a pain symptom entry and tracking process 200 for providing a body location, an intensity, and a type of bodily pain and storing the body location, intensity, and type of pain in a chronic pain database in some embodiments. As mentioned for the meal entry and food identification and storage process 100 described above by reference to FIG. 1, the pain symptom entry and tracking process 200 in this figure is performed by the chronic pain and food trigger tracking app (mobile app or web app) running on a mobile device, another computing device, or other electronic system.

In some embodiments, the pain symptom entry and tracking process 200 starts by user interaction in a user profile settings section of the chronic pain and food trigger tracking app, which includes an option for a primary body location of pain (at 205). Examples of primary body locations include feet, legs, hands, arms, torso, pelvic area, shoulders, neck, and head, among other body locations. Also, pain experienced by a user need not be limited to only physical pain. For example, if the user indicates the primary body location of pain is his or her head, the 'pain' being experienced may be a physically-manifested pain (e.g., a migraine headache) or a mental pain (e.g., stress, anxiety arising from a feeling of being overwhelmed or lost, or fear that triggers a fight or flight response, etc.). Next, a figure of a body (a body model) is visually output, by the chronic pain and food trigger tracking app, onto a screen of the user's device. The body model is configured to enable user interaction. Thus, the user clicks on, touches (for a touchscreen), or otherwise selects a body part of the body model to indicate a location of pain (at 210). After selecting the body part as the location of pain (at 210), the pain symptom entry and tracking process 200 proceeds to a step at which the user is prompted, by the chronic pain and food trigger tracking app, to select a pain intensity (at 215) at the selected body part location of pain. In some embodiments, the chronic pain and food trigger tracking app visually outputs an interactive slider tool that enables the user to move the slider along a range of pain intensities. The range of pain intensities in some embodiments is a numeric scale from zero to ten (0-10) with zero being an indication of no pain and ten being an indication of the most pain. Notably, the slider tool and the numeric scale are design choices that can be implemented in other forms, such as a list of pain intensities from which the user may select a particular pain intensity or a range/scale from zero to one-hundred or a range/scale of color variation from blue (no pain) to red (most pain), or other variations.

After the user selects the pain intensity (at 215), the pain symptom entry and tracking process 200 proceeds to the next step at which the user is prompted, by the chronic pain and food trigger tracking app, to select a pain type (at 220). The chronic pain and food trigger tracking app may output a list of pain types from which the user may select a particular pain type (e.g., throbbing pain, dull pain, sharp pain, migraine, stress, anxiety, etc.). In some embodiments, the chronic pain and food trigger tracking app is configured to filter the list of pain types which are displayed to pain types that are associated with the primary body location of pain. For example, if the user selects the head as the primary body location of pain, the list of pain types may be filtered down to physical head pains (e.g., migraines, other types of headaches, etc.) and mental head pains (e.g., stress, anxiety, depression, etc.), while a selection of the eyes as the primary body location of pain would list pain types such as eye-pressure, vision issues, etc. In other embodiments, the user may be presented with a text entry field to enter a free-form textual description of the type of pain.

Next, the pain symptom entry and tracking process 200 proceeds to a step at which the user is prompted, by the chronic pain and food trigger tracking app visually outputting a checkbox, to indicate whether the pain is from a known injury (at 225). Similarly, the user is prompted, by the chronic pain and food trigger tracking app visually outputting another checkbox, to indicate whether the pain is from a known trigger (at 230). When the user selects the checkbox indicating that the pain is from a known trigger, the pain symptom entry and tracking process 200 of some embodiments updates a training model customized for the user to include the known trigger (at 235), followed by storing (at 240) the user's pain body location, pain type, and pain intensity at a given time in a user pain database (at 242). On the other hand, when the user has not selected the checkbox indicating that the pain is from a known trigger (at 230), the pain symptom entry and tracking process 200 skips the step for updating the user's training model (at 235) and, instead, proceeds directly to the step for storing (at 240) the user's pain body location, pain type, and pain intensity at the given time in the user pain database (at 242).

After storing the user's pain data, the pain symptom entry and tracking process 200 determines (at 245) whether this is the first time the user has entered pain information and also whether the profile settings for the user do not have a primary pain body location set. This is critical to determine the extent of chronic, recurring pain on the user's body. When it is determined (at 245) that this not the first time the user entered pain information and the profile settings for the user affirmatively does indicate that the user has set a primary pain body location, then the pain symptom entry and tracking process 200 ends.

On the other hand, when it is determined (at 245) that this is the first time the user has entered pain information, whether or not the profile settings do not have a primary pain body location set, then the pain symptom entry and tracking process 200 sets a counter for the body pain location (at 250) in the profile settings to a value of one ('1'). If the user did not specify the location, a pain body location is determined by the chronic pain and food trigger tracking app and used as the body pain location in the profiles settings. The pain symptom entry and tracking process 200 then determines (at 255) whether the user has indicated more body locations with pain. When there are no more body locations with pain, the pain symptom entry and tracking process 200 ends. However, when there are affirmatively more body locations with pain ('YES'), the pain symptom entry and tracking process 200 proceeds to update (or increment) the counter value of all body pain location (at 260) and to also show the primary pain body location as set by the user or, when not specified by the user, the primary pain body location as determined by the chronic pain and food trigger tracking app. Then the pain symptom entry and tracking process 200 transitions back to the step at which the user selects, from the user body model within the chronic pain and food trigger tracking app, the body part experiencing the pain (at 210) and continuing forward through the remaining steps 215-255 until the pain symptom entry and tracking process 200 ends.

Figure 3A:
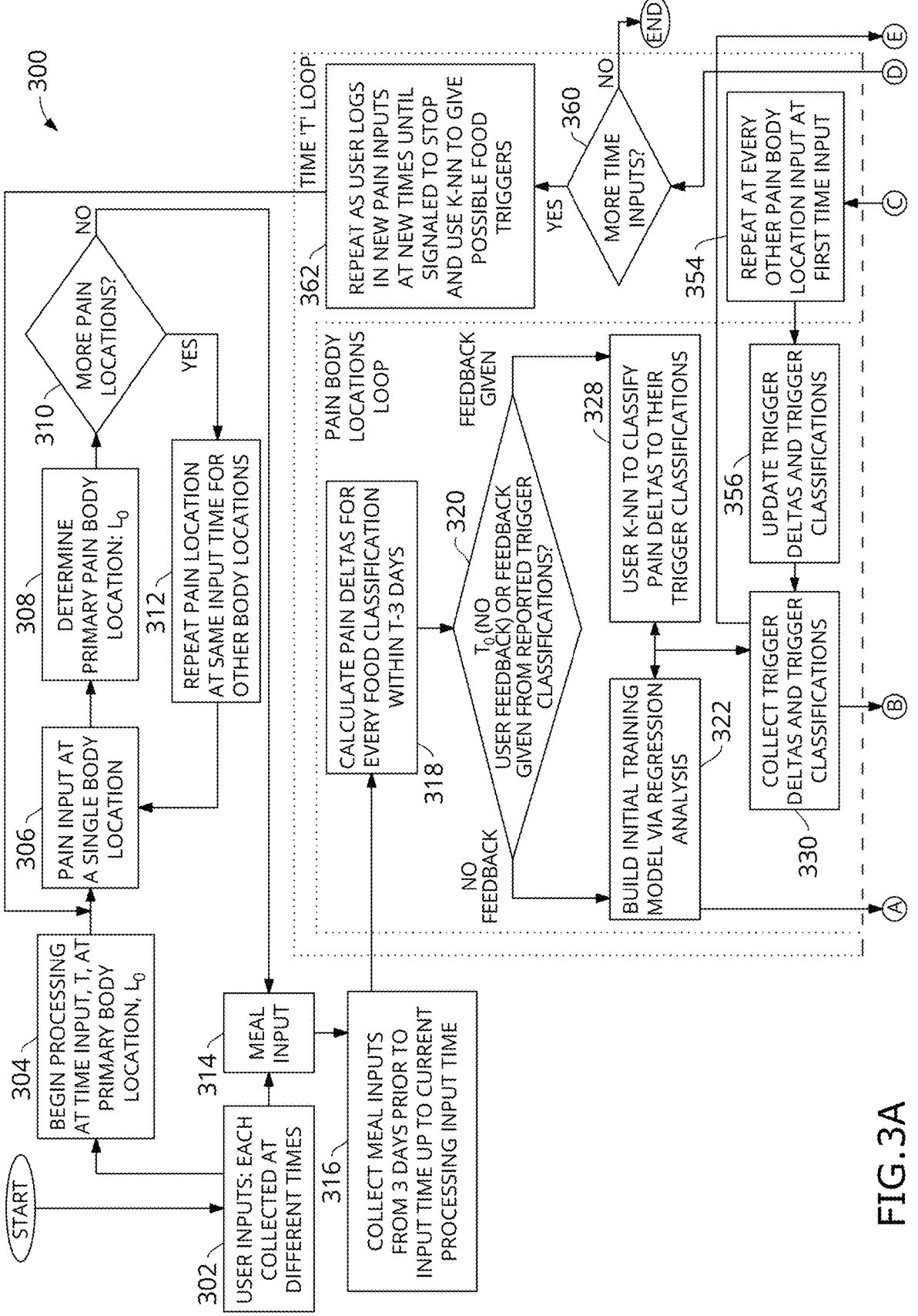
FIGS. 3A and 3B conceptually illustrate a time-monitored chronic pain and food trigger identification machine learning process for meal and pain input processing in some embodiments.
Figure 3B:
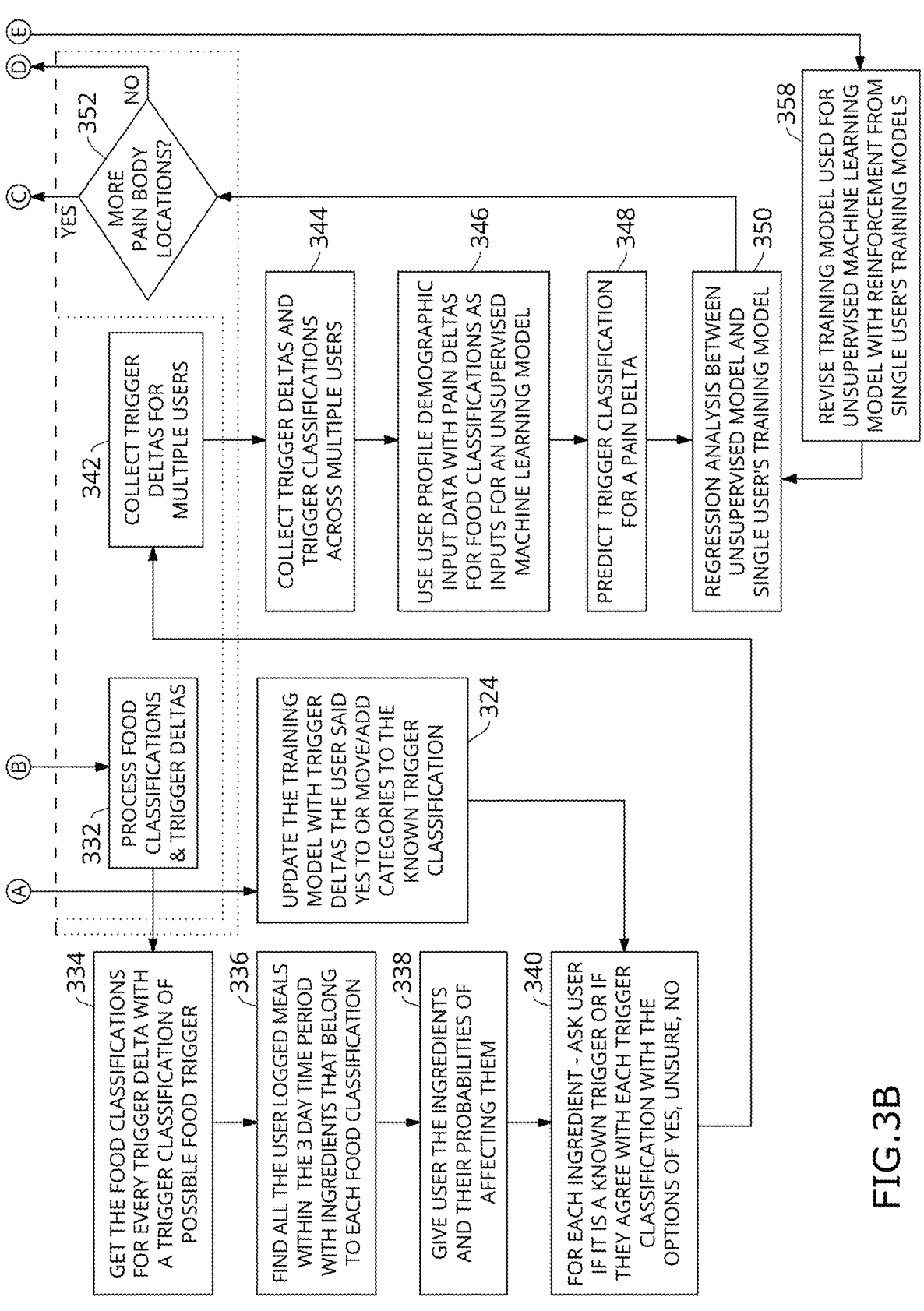

By way of example, FIG. 3 conceptually illustrates a time-monitored chronic pain and food trigger identification machine learning process 300 for meal and pain input processing in some embodiments. The time-monitored chronic pain and food trigger identification machine learning process 300 is performed in part by the chronic pain and food trigger tracking app (through which the user interacts to input food and pain information) and a backend chronic pain and food trigger tracking processing system. The backend chronic pain and food trigger tracking processing system may be, for example, a background process of the chronic pain and food trigger tracking app. Alternatively, the backend chronic pain and food trigger tracking processing system may be, for example, a chronic pain and food trigger tracking cloud application service hosted by a backend chronic pain and food trigger tracking server of the machine-learning based, interactive chronic pain and food trigger tracking system. An example of a chronic pain and food trigger tracking cloud application service hosted by a backend chronic pain and food trigger tracking server of the machine-learning based, interactive chronic pain and food trigger tracking system is described below, by reference to FIG. 5.

The time-monitored chronic pain and food trigger identification machine learning process 300 shown in FIG. 3 starts when the user provides pain data input (at 302) and the pain data input is received (collected) by the chronic pain and food trigger tracking app a different times (at 302). For instance, the user enters a first pain at a first body location at 8:05 AM on a first day and a second pain at a second body location at the same time 8:05 AM on the first day, followed by entry of a third pain at the first body location at a different time 12:30 PM on the first day, and a fourth pain at a third body location at 6:00 PM on the first day.

The time-monitored chronic pain and food trigger identification machine learning process 300 begins processing the data (at 304) and time ('T') at a primary body location ('$I_0$'). Next, the pain input at a single body location (at 306) is evaluated by the time-monitored chronic pain and food trigger identification machine learning process 300 to determine (at 308) where to set the primary pain body location ('$I_0$') experienced at the time ('T'). Once determined, the time-monitored chronic pain and food trigger identification machine learning process 300 sets the primary pain body location for $I_0$ to the single body location of the pain input. Then the time-monitored chronic pain and food trigger identification machine learning process 300 determines whether additional pain locations have been collected from the user input (at 310). When there are more pain locations to consider ('YES'), the time-monitored chronic pain and food trigger identification machine learning process 300 repeats pain location processing (at 312) for other body locations experiencing pain at the same time input ('T'), transitioning back to the step for pain input at the single body location (at 306), in this case the single body location being a different body location experiencing pain at the same input time ('T'). On the other hand, when it is determined (at 310) that there are no more pain locations ('NO'), the time-monitored chronic pain and food trigger identification machine learning process 300 proceeds to a step for meal input processing (at 314).

In some embodiments, meal input (at 314) is processed according to the meal entry and food identification and storage process 100 and stored in the composite food database persistent storage (at 140), described above by reference to FIG. 1. The meal input (at 314) may be performed as many times as the user eats and may extend over a lengthy period of time, in the order of days or weeks. With such meal input (at 314) processed and stored in the composite food database persistent storage, the time-monitored chronic pain and food trigger identification machine learning process 300 collects (retrieving from the composite food database persistent storage) the composite records of meal inputs from several days prior to the input time ('T') and up to a current processing input time (at 316). In some embodiments, the time-monitored chronic pain and food trigger identification machine learning process 300 retrieves/collects the composite records of meal inputs from three days prior to the input time ('T') and up to the current processing input time (at 316).

After collecting the meal inputs from time period (e.g., T–3 days), the time-monitored chronic pain and food trigger identification machine learning process 300 enters a time T loop that is repeated as a cycle of steps performed at each time input (e.g., $T_0$, $T_1$, $T_2$, . . . , $T_N$). Also, the time-monitored chronic pain and food trigger identification machine learning process 300 enters a pain body locations loop that is repeated for each pain body location entered by the user at a given time (e.g., two pain body locations entered at time $T_0$, one pain body location entered at time $T_1$, two pain body locations entered at time $T_2$, etc.).

Thus, entering the time T loop and the pain body locations loop, the time-monitored chronic pain and food trigger identification machine learning process 300 calculates pain deltas (at 318) for every food classification within the several days time period (e.g., T–3 days). The time-monitored chronic pain and food trigger identification machine learning process 300 then determines (at 320) whether there is any user feedback for a reported trigger classification at time $T_N$ (at this point in the description, the first time, To) or no user feedback at all. When there is no user feedback determined (at 320), the time-monitored chronic pain and food trigger identification machine learning process 300 proceeds to a step for building an initial training model via regression analysis (at 322), which involves several steps performed in parallel, or contemporaneously with each other, including (i) processing trigger deltas (at 324) which involves either (or both) updating the training model with trigger deltas accepted by the user or moving/adding categories to the known trigger classification (at 324) and (ii) collecting trigger deltas and trigger classifications (at 330).

On the other hand, when feedback is determined (at 320) to be given by the user, the time-monitored chronic pain and food trigger identification machine learning process 300 proceeds to a step for using a machine learning or deep learning algorithm, such as the K-NN machine learning algorithm, to classify pain deltas to their respective trigger classifications (at 328) followed by collecting trigger deltas and trigger classifications (at 330).

In some embodiments, the step for collecting trigger deltas and trigger classifications (at 330) proceeds to multiple parallel steps including (i) processing food classifications and trigger deltas (at 332) and (ii) revising a training model used for an unsupervised machine learning model with reinforcement learning from the user's training model, which is a single user's training model (at 358).

Turning back to the step for updating the training model with trigger deltas the user accepted (at 324) or moving/adding categories to the known trigger classification (at 324), the time-monitored chronic pain and food trigger identification machine learning process 300 proceeds to a step at which the user is prompted to indicate, for each ingredient, whether the ingredient is a known trigger or whether the user agrees with each trigger classification (at 340). In some embodiments, the user selects an option such as 'YES', 'NO', or 'UNSURE' to agree, disagree, or otherwise indicate uncertainty as to whether the ingredient is a known trigger. With the trigger deltas sorted out for this user, the time-monitored chronic pain and food trigger identification machine learning process 300 proceeds to collect trigger deltas for multiple user (at 342). Several steps for collecting trigger deltas for multiple users (at 342) are described further below.

Now turning back to the step for processing food classifications and trigger deltas (at 332), the time-monitored chronic pain and food trigger identification machine learning process 300 proceeds to retrieve the food classifications for every trigger delta with a trigger classification of a possible food trigger (at 334). With the food classifications retrieved, the time-monitored chronic pain and food trigger identification machine learning process 300 finds, within a time period extending back several days, all of the user-logged meals with ingredients that belong to each classification (at 336). In some embodiments, the several days time period extends back three days from input time 'T'. In some embodiments, the time-monitored chronic pain and food trigger identification machine learning process 300 finds all of the user-logged meals by retrieving the composite food records stored in the composite food database for the extended time period (e.g., T–3 days up to the current input time 'T').

After retrieving all of the meals and ingredients going back over the several days time period, the time-monitored chronic pain and food trigger identification machine learning process 300 proceeds to a step for providing, to the user in the chronic pain and food trigger tracking app, the ingredients and their respective probabilities of affecting them (at 338). The probabilities provide a prediction as to culprits which may be involved in flare-ups of chronic pain symptoms felt by the user and are provided as trigger classifications. However, the user may not agree with all of the trigger classifications. Thus, the time-monitored chronic pain and food trigger identification machine learning process 300 proceeds the step at which the user is prompted to indicate, for each ingredient, whether the ingredient is a known trigger or whether the user agrees with each trigger classification (at 340), selecting one of the options (e.g., 'YES', 'NO', or 'UNSURE') to agree, disagree, or otherwise indicate uncertainty as to whether the ingredient is a known trigger. Then the time-monitored chronic pain and food trigger identification machine learning process 300 proceeds to the step for collecting trigger deltas for multiple user (at 342) which involves several additional steps, as described next.

In some embodiments, the time-monitored chronic pain and food trigger identification machine learning process 300 collects trigger deltas for multiple users (at 342) by collecting trigger deltas and trigger classifications across the multiple users (at 344). Then the time-monitored chronic pain and food trigger identification machine learning process 300 utilizes user profile demographic information for each user among the multiple users with pain deltas for food classifications as inputs for the unsupervised machine learning model (at 346). An example of unsupervised machine learning is described below, by reference to FIG. 7. Next, the time-monitored chronic pain and food trigger identification machine learning process 300 predicts a trigger classification for each pain delta (at 348) and then performs regression analysis between the unsupervised machine learning model and the single user's training model (at 350).

Notably, the regression analysis between the unsupervised machine learning model and the single user's training model (at 350) is performed by the time-monitored chronic pain and food trigger identification machine learning process 300 after the step for revising the training model used for the unsupervised machine learning model with reinforcement learning from the single user's training model (at 358).

After completing the regression analysis between the unsupervised machine learning model and the single user's training model (at 350), the time-monitored chronic pain and food trigger identification machine learning process 300 determines (at 352) whether there are any more pain body locations to evaluate.

When there are more pain body locations to evaluate ('YES'), the time-monitored chronic pain and food trigger identification machine learning process 300 repeats the evaluation and processing for every other pain body location entered by the user at the input time (at 354). For instance, if this cycle is processing all pain body inputs at time $T_0$, then there may be two pain body locations which were entered at that time, but other time-entered pain body locations are not evaluated in this repeated step, but only get processed at the next time entry (e.g., $T_N$). Thus, the time-monitored chronic pain and food trigger identification machine learning process 300 remains in the pain body locations loop (and also in the time T loop).

Repeating the evaluation and processing for every other pain body location entered by the user at the input time (at 354) is followed by the time-monitored chronic pain and food trigger identification machine learning process 300 updating the trigger deltas and trigger classifications (at 356), followed by collecting the trigger deltas and trigger classifications (at 330). The step for collecting the trigger deltas and trigger classifications (at 330) is followed by parallel processing of multiple different steps by the time-monitored chronic pain and food trigger identification machine learning process 300. As noted above the parallel steps of processing food classifications and trigger deltas (at 332) and subsequent steps is/are performed in parallel with the time-monitored chronic pain and food trigger identification machine learning process 300 revising the training model used for the unsupervised machine learning model with reinforcement learning (at 358) based on the single user's training model, as described above.

Turning back to the determination (at 352), when there are no more pain body locations to evaluate ('NO'), the time-monitored chronic pain and food trigger identification machine learning process 300 exits the pain body locations loop and moves forward to a step for determining (at 360) whether there are more time inputs remaining. When there are no more time inputs remaining ('NO'), the time-monitored chronic pain and food trigger identification machine learning process 300 ends. However, when there are more time inputs remaining ('YES'), the time-monitored chronic pain and food trigger identification machine learning process 300 exists the time T loop and proceeds to the next time input, repeating the time T loop as the user enters new pain inputs at new times (at 362). The repeating steps start by the time-monitored chronic pain and food trigger identification machine learning process 300 reverting back to the step for pain input by the user at a single body location (at 306) and continuing forward as described above. In some embodiments, the user repeats the process of entering new pain inputs at new times (at 362) until signaled to stop or until the time-monitored chronic pain and food trigger identification machine learning process 300 ends (such as when there are no remaining time inputs to process). In some embodiments, repeating the process for entering new pain inputs at new times (at 362) uses the machine learning algorithm or deep learning algorithm (e.g., K-NN machine learning algorithm) to identify possible food triggers.

Figure 4A:
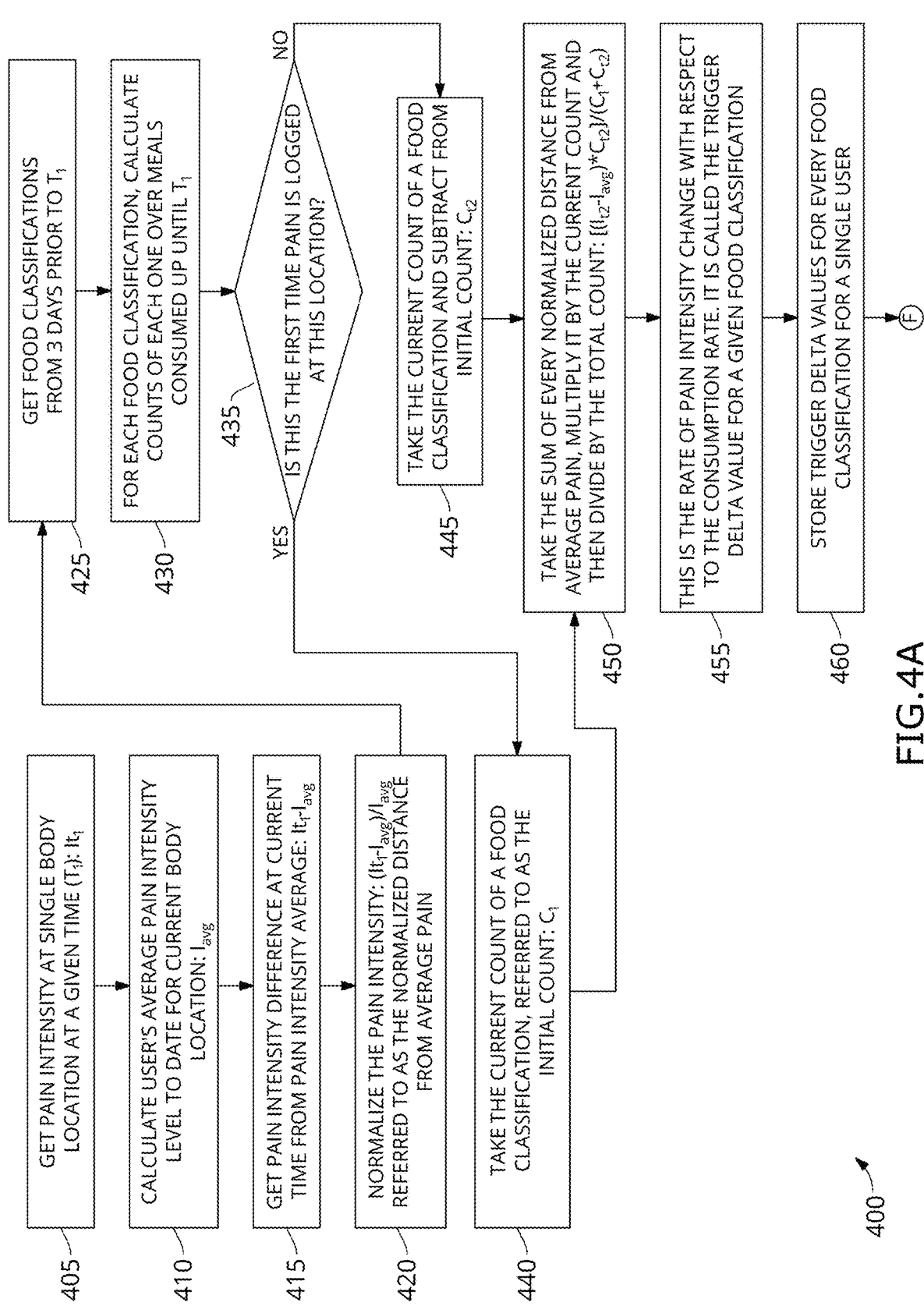
FIGS. 4A and 4B conceptually illustrate a time-monitored pain intensity and trigger delta value identification machine learning process that involves single user regression analysis and a machine learning algorithm to identify a trigger delta value expressing a rate of change in pain intensity for a consumption rate of food with a food classification in some embodiments.
Figure 4B:
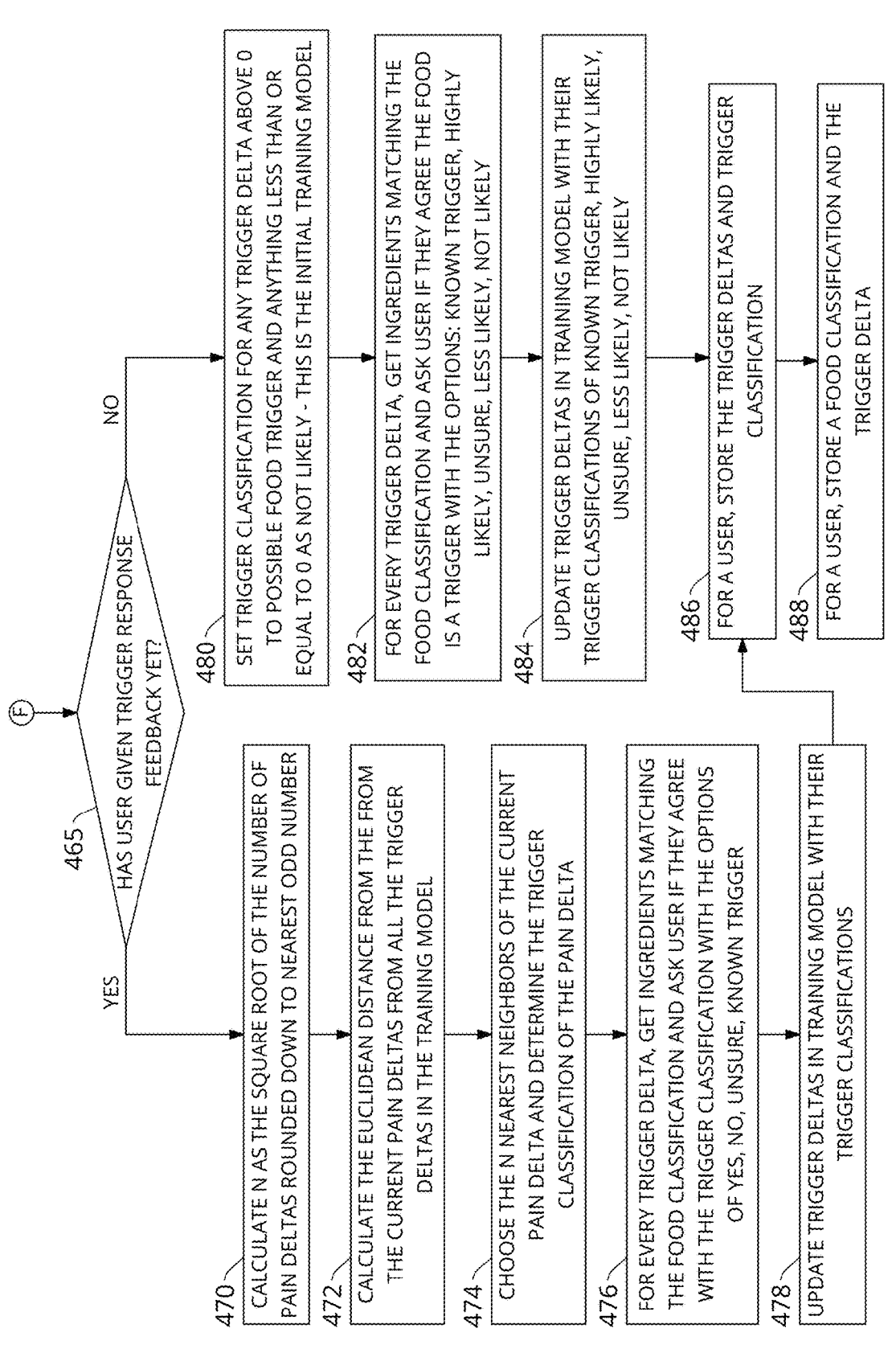

By way of example, FIG. 4 conceptually illustrates a time-monitored pain intensity and trigger delta value identification machine learning process 400 that involves single user regression analysis and a machine learning algorithm (also referred to as a deep learning algorithm) to identify a trigger delta value expressing a rate of change in pain intensity for a consumption rate of food with a food classification in some embodiments. The machine learning algorithm may be any suitable machine learning algorithm. In a preferred embodiments, the machine learning algorithm comprises the K-NN machine learning algorithm. Also, the time-monitored pain intensity and trigger delta value identification machine learning process 400 is performed by a backend chronic pain and food trigger tracking processing system and deep learning processing system/unit that is either embedded in, or communicably connect to, the backend chronic pain and food trigger tracking processing system. An example of a deep learning processing unit communicably connected to a backend chronic pain and food trigger tracking processing system is described below, by reference to FIG. 5 and another example of a deep learning processing server unit is described further below, by reference to FIG. 7.

As shown in FIG. 4, the time-monitored pain intensity and trigger delta value identification machine learning process 400 starts by receiving (or getting) the pain intensity at a single body location at a given time (at 405). The pain intensity is input by the user on the user body model through the chronic pain and food trigger tracking app. The pain intensity is denoted as '$I_{t1}$' and the given time is denoted as '$T_1$' for purposes of explanation. Next, the time-monitored pain intensity and trigger delta value identification machine learning process 400 calculates the user's average pain intensity level to date for the current, single body location (at 410). The average pain intensity level is denoted as '$I_{avg}$' for purposes of explanation.

After calculating $I_{avg}$ (at 410), the time-monitored pain intensity and trigger delta value identification machine learning process 400 determines (or gets) the difference in pain intensity (at 415) between $I_{t1}$ at the current time $T_1$ and $I_{avg}$ as calculated. In some embodiments, the difference is expressed as $I_{t1}-I_{avg}$. Next, the time-monitored pain intensity and trigger delta value identification machine learning process 400 normalizes the pain intensity (at 420). In some embodiments, the normalization of pain intensity is expressed as a calculation of $(I_{t1}-I_{avg})/I_{avg}$ and is referred to the normalized distance from average pain.

With the pain intensity data processed, the time-monitored pain intensity and trigger delta value identification machine learning process 400 moves forward a step for retrieving (or getting) food classifications (at 425) from the several days prior to the given time ('$T_1$'). In some embodiments, the time-monitored pain intensity and trigger delta value identification machine learning process 400 gets food classifications for the three days prior to the given time, expressed as $T_1-3$ days. Then the time-monitored pain intensity and trigger delta value identification machine learning process 400 counts (at 430) the number of occurrences of each food classification over the time span ($T_1-3$ days) for the meals consumed by the user (that is, the meals input by the user during the time span, $T_1-3$ days).

With respect to the single body location associated with the pain intensity $I_{t1}$ at the given time $T_1$, the time-monitored pain intensity and trigger delta value identification machine learning process 400 determines (at 435) whether this occurrence is the first time pain was logged at this body location for the user. When the pain intensity $I_{t1}$ at the given time $T_1$, is determined (at 435) to be the first time that pain is logged by the user at this body location ('YES'), the time-monitored pain intensity and trigger delta value identification machine learning process 400 of some embodiments takes the current count of food classifications as the initial count of food classifications (at 440). The initial count is referred to as $C_1$. However, when the pain intensity $I_{t1}$ at the given time $T_1$, is not the first time that pain was logged by the user at this body location ('NO'), the time-monitored pain intensity and trigger delta value identification machine learning process 400 instead takes the current count of food classifications and subtracts from a (previously determined) initial count of food classifications (at 445). This is expressed as $C_{t2}$. Next, the time-monitored pain intensity and trigger delta value identification machine learning process 400 multiplies the sum of every normalized distance from average pain by the current count and divides the resulting product by the total count (at 450). This is expressed as $[(I_{t1}-I_{avg})\times C_{t2}]/(C_1-C_{t2})$. This expression (i.e., $[(I_{t1}-I_{avg})\times C_{t2}]/(C_1-C_{t2})$) represents the rate of change in pain intensity with respect to the user's food consumption rate (at 455) and is referred to as the trigger delta value for a given food classification.

After the rate of change in pain intensity is determined for all relevant food classifications for the user, the time-monitored pain intensity and trigger delta value identification machine learning process 400 stores the trigger delta values (at 460) and proceeds forward to a step for determining (at 465) whether the user has given trigger response feedback yet. When the user has provided trigger response feedback ('YES'), the time-monitored pain intensity and trigger delta value identification machine learning process 400 proceeds to a series of steps starting with calculating a number 'N' as the square root of the number of pain deltas, rounded down to the nearest odd number (at 470), followed by several subsequent steps described below. On the other hand, when the user has not provided trigger response feedback ('NO'), the time-monitored pain intensity and trigger delta value identification machine learning process 400 proceeds to a different series of steps starting with setting a trigger classification, for each trigger delta value greater than zero, to a possible food trigger for an initial training model (at 480), followed by several subsequent steps as described further below. In this case, the time-monitored pain intensity and trigger delta value identification machine learning process 400 does not consider trigger delta values less than or equal to zero as in need of setting a trigger classification to a food trigger, as such zero or negative values for trigger deltas are unlikely to be triggered by food.

Turning back to the series of steps starting with calculating a number 'N' as the square root of the number of pain deltas, rounded down to the nearest odd number (at 470), the time-monitored pain intensity and trigger delta value identification machine learning process 400 of some embodiments calculates the Euclidean distance from the current pain deltas to all the trigger deltas in the training model (at 472). Next, the time-monitored pain intensity and trigger delta value identification machine learning process 400 chooses the N nearest neighbors of the current pain delta (i.e., the number N calculated at 470, above) and determines the trigger classification of the pain delta (at 474). Then, for every trigger delta, the time-monitored pain intensity and trigger delta value identification machine learning process 400 retrieves (or gets) the ingredients matching the food classification and prompts the user indicate whether the user agrees with the trigger classification (at 476). For instance, the time-monitored pain intensity and trigger delta value identification machine learning process 400 may trigger the chronic pain and food trigger tracking app to visually output a prompt with user-selectable options of 'YES' to express agreement with the trigger classification, 'NO' to express disagreement with the trigger classification, 'UNSURE' to express uncertainty as to whether the trigger classification is correct or not, and 'KNOWN TRIGGER' to express user's belief that this is already known trigger. Then the time-monitored pain intensity and trigger delta value identification machine learning process 400 updates the trigger deltas in the training model (at 478) with their trigger classifications. Next, the time-monitored pain intensity and trigger delta value identification machine learning process 400 stores the trigger deltas and trigger classifications for the user (at 486) and then stores the food classification and the trigger delta for the user (at 488).

Now referring back to the different series of steps starting with setting the trigger classification for each trigger delta value greater than zero to a possible food trigger for the initial training model (at 480), the time-monitored pain intensity and trigger delta value identification machine learning process 400 of some embodiments retrieves (or gets), for every trigger delta, ingredients matching the food classification (at 482) and prompts the user to indicate whether the user agrees that the food is a trigger. For instance, the time-monitored pain intensity and trigger delta value identification machine learning process 400 may trigger the chronic pain and food trigger tracking app to visually output a prompt with user-selectable options of 'KNOWN TRIGGER', 'HIGHLY LIKELY', 'UNSURE', 'LESS LIKELY', and 'NOT LIKELY' to indicate a level of agreement by the user that the food is a trigger or not. Next, time-monitored pain intensity and trigger delta value identification machine learning process 400 updates the trigger deltas in the training model with their trigger classifications (at 484) with designations including 'KNOWN TRIGGER', 'HIGHLY LIKELY', 'UNSURE', 'LESS LIKELY', and 'NOT LIKELY'. Then the time-monitored pain intensity and trigger delta value identification machine learning process 400 stores the trigger deltas and trigger classifications for the user (at 486) and then stores the food classification and the trigger delta for the user (at 488). After storing the trigger deltas and trigger classifications and the food classification and trigger delta for the user, the time-monitored pain intensity and trigger delta value identification machine learning process 400 ends.

Figure 5:
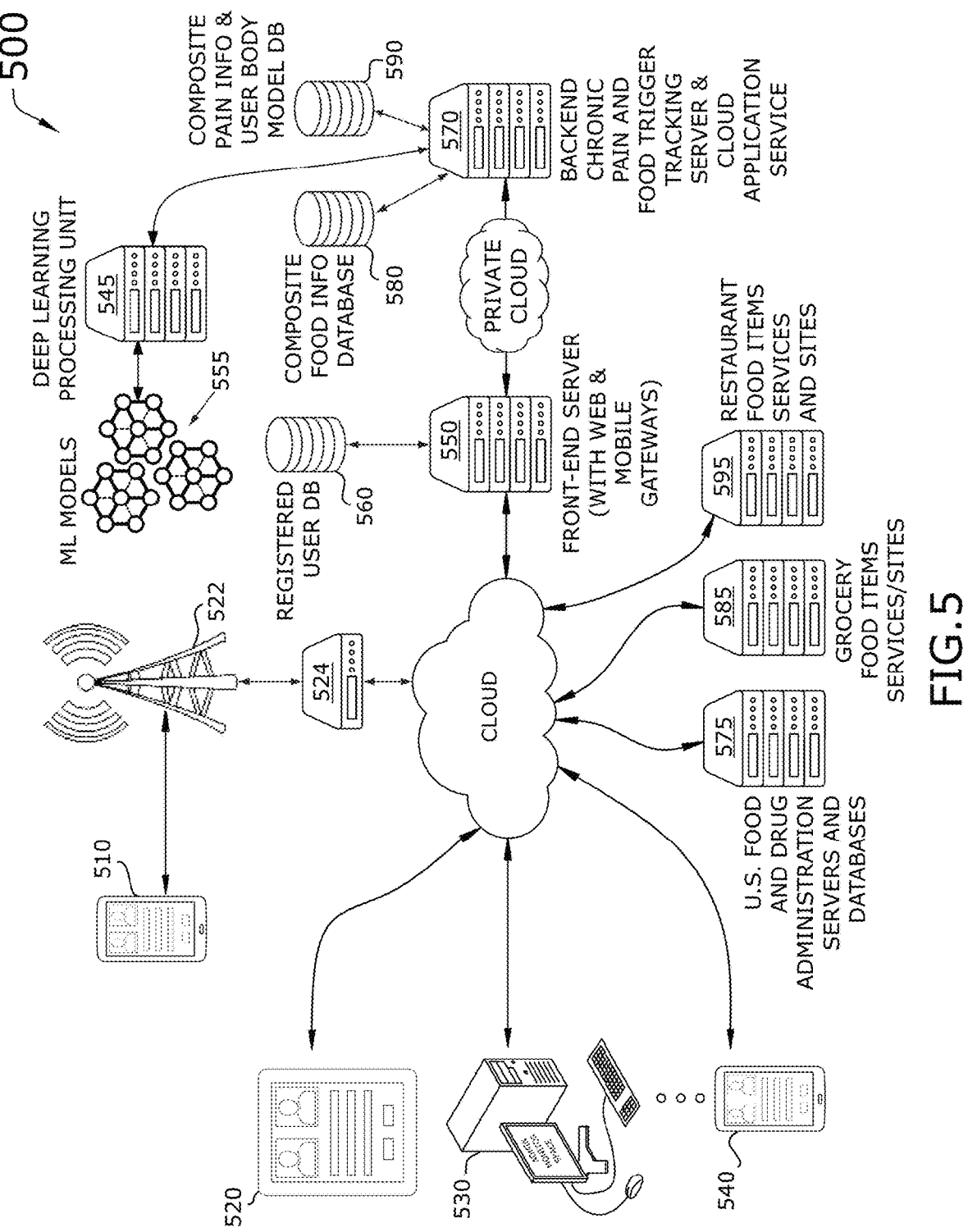
FIG. 5 conceptually illustrates a network architecture of a machine-learning based, interactive chronic pain and food trigger tracking system that hosts a chronic pain and food trigger tracking cloud application service in some embodiments.

By way of example, FIG. 5 conceptually illustrates a network architecture of a machine-learning based, interactive chronic pain and food trigger tracking system 500. As shown in this figure, the machine-learning based, interactive chronic pain and food trigger tracking system 500 provides a front-end server 550 with web and mobile gateways and a backend chronic pain and food trigger tracking server 570 that hosts a chronic pain and food trigger tracking cloud application service. The machine-learning based, interactive chronic pain and food trigger tracking system 500 includes several other systems and hardware components configured to track food intake and chronic pain symptoms and to identify corresponding food and pain triggers that cause new pain or change intensity of existing chronic pain in a person. Specifically, the machine-learning based, interactive chronic pain and food trigger tracking system 500 includes a deep learning processing unit 545 that is communicably connected to the backend chronic pain and food trigger tracking server 570. In connection with the deep learning processing unit 545 are machine learning models 555 to which the deep learning processing unit 545 performs deep learning algorithms and/or machine learning algorithms, such as single user regression analysis and the K-NN machine learning algorithm described above, by reference to FIG. 4. The deep learning processing unit 545 also performs machine learning tasks, such as initial machine learning model training and periodic retraining. For instance, the deep learning processing unit 545 provides food intake, time, and pain data received from each individual user to a deep learning algorithm and corresponding model that is trained to identify food and pain triggers for that user. A more detailed example of a deep learning processing unit is described below, by reference to FIG. 7.

Other components of the machine-learning based, interactive chronic pain and food trigger tracking system 500 include a registered user database 560 communicably connected to the front-end server 550, a composite food information database 580 communicably connected to the backend chronic pain and food trigger tracking server 570, and a composite pain information & user body model database 590 also communicably connected to the backend chronic pain and food trigger tracking server 570. In some embodiments, the registered user database 560 is configured to store user information required for registration and authenticated access (via login with user credentials, such as username/password, two-factor authentication, etc.). The registered user database 560 also ensures that custom user body models and associated pain information and food information is stored exclusively for each individual registered user. In some embodiments, the composite food information database 580 is configured to store food intake data input by each user, time of meal data, and related food information including text data input by the user, textual information retrieved from external services and sites, taxonomical classification data provided by the backend chronic pain and food trigger tracking server 570, food information retrieved from government sites, and images of meals, food items, ingredients, etc., as captured with a camera and uploaded by the user. In some embodiments, the composite pain information & user body model database 590 is configured to store all user-provided pain information, including the pain symptoms, dates of entry, dates of experiencing the pain symptoms, intensity of the pain, type of pain, location of the pain on the body, and the custom user body model for each individual user.

In some embodiments, external services and sites are accessible to the machine-learning based, interactive chronic pain and food trigger tracking system 500. As shown in this figure, the external services and sites include U.S. Food and Drug Administration (FDA) servers and databases 575, grocery food items services and sites 585, and restaurant food items services and sites 595, each of which are in network connection (via the "cloud") with the machine-learning based, interactive chronic pain and food trigger tracking system 500.

In some embodiments of the machine-learning based, interactive chronic pain and food trigger tracking system 500, the chronic pain and food trigger tracking cloud application service hosted by the backend chronic pain and food trigger tracking server 570 is accessible to computing devices operated by end users who are seeking to track food intake and pain symptoms and identify food triggers that exacerbate, increase, or intensify chronic pain. The computing devices would have the chronic pain and food trigger tracking app installed, thereby enabling their respective users to access and interact with the chronic pain and food trigger tracking cloud application service. The computing devices shown in this figure include a first mobile device 510, a tablet computing device 520, a desktop computer 530, and a second mobile device 540. A user operating the first mobile device 510 connects to the front-end server 550 of the machine-learning based, interactive chronic pain and food trigger tracking system 500 by way of a wireless connection to the wireless communication point 522 and through a gateway device 524, finally connecting over the Internet (or "cloud") to the front-end server 550. The user may wish to register in order to track food intake and pain symptoms over time, however, registration is not required to obtain certain benefits of the chronic pain and food trigger tracking app, such as DBT-style guidance for managing pain symptoms. However, if the user wishes to track food intake and pain symptoms over time to identify possible food triggers for their pain, then registration is performed at the front-end server. The registration details for the user will be encrypted and stored in the registered agent database 560 so that subsequent connections by the registered user only require user login. Then all previously input food and pain data, as well as the user's custom body model can be retrieved from the backend and loaded into the chronic pain and food trigger tracking app. Note, while the figure only illustrates the first mobile device 510 connecting via the wireless communication point 522 and through the gateway 524, it should be understood that any of the mobile devices (e.g., the tablet computing device 520 and the second mobile device 540) can connect wirelessly by cellular or other mobile device signal to the wireless communication point 522 and through the gateway 524 to establish a network connection with the front-end server 550, and thereby access the chronic pain and food trigger tracking cloud application service. On the other hand, the tablet computing device 520, the desktop computer 530, and the second mobile device 540 are shown connecting to the front-end server 550 through the cloud. In this sense, these devices may be wired or wireless and connect through such means as Ethernet cables, wireless communication protocols, such as WiFi, etc.

Many of the above-described features and applications are implemented as software processes that are specified as a set of instructions recorded on a computer readable storage medium (also referred to as computer readable medium or machine readable medium). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

In this specification, the term "software" is meant to include firmware residing in read-only memory or applications stored in magnetic storage, which can be read into memory for processing by a processor. Also, in some embodiments, multiple software inventions can be implemented as sub-parts of a larger program while remaining distinct software inventions. In some embodiments, multiple software inventions can also be implemented as separate programs. Finally, any combination of separate programs that together implement a software invention described here is within the scope of the invention. In some embodiments, the software programs, when installed to operate on one or more electronic systems, define one or more specific machine implementations that execute and perform the operations of the software programs.

Figure 6:
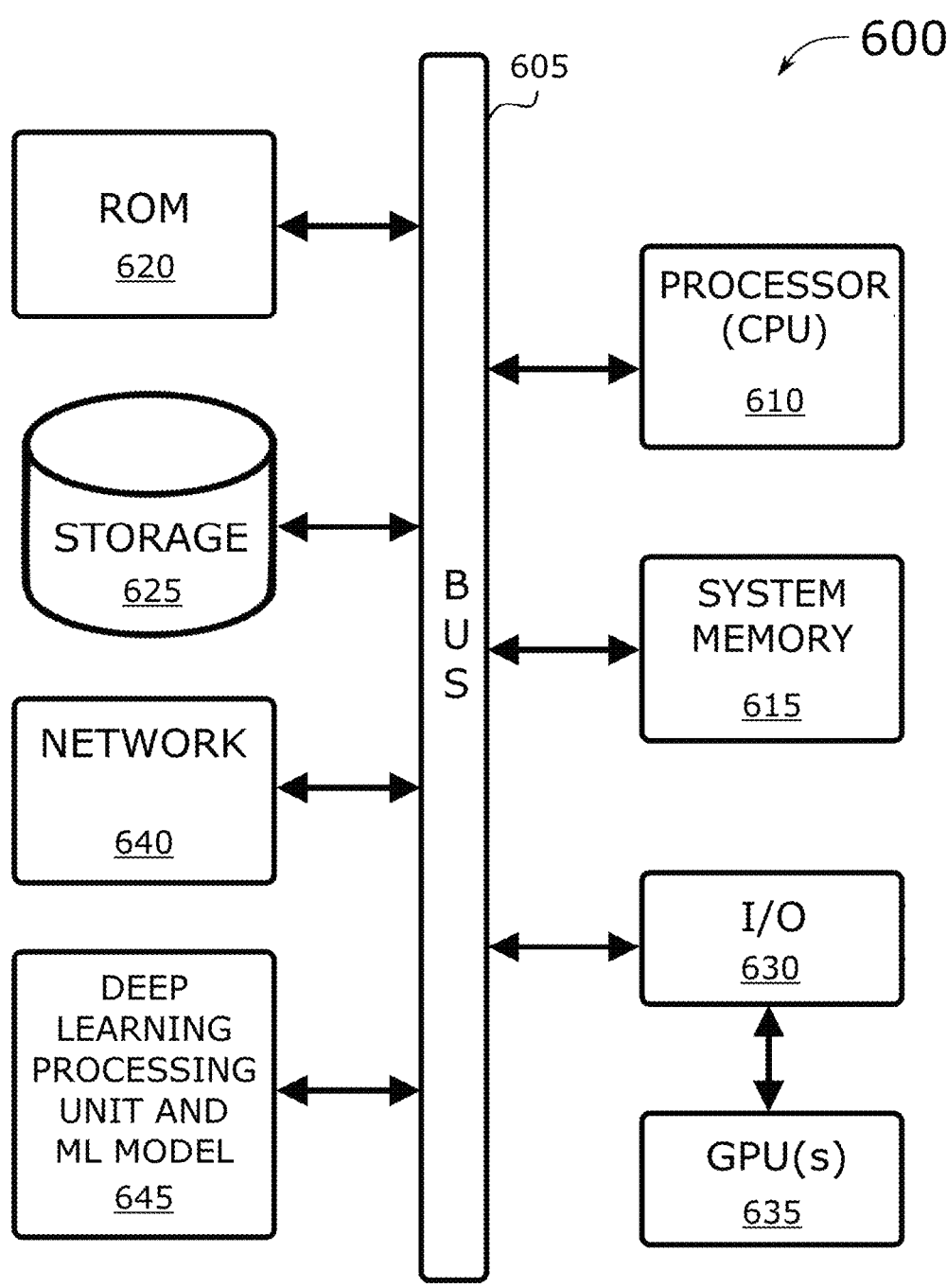
FIG. 6 conceptually illustrates an electronic system with which some embodiments of the invention are implemented.

By way of example, FIG. 6 conceptually illustrates an electronic system 600 with which some embodiments of the invention are implemented. The electronic system 600 may be a computer (such as a desktop computer, a personal computer (PC), or a laptop computer), a phone (such as a smart phone), a personal digital assistant (PDA), a single board computer (SBC), a server computer, a server configured to perform AI and machine learning, or any other sort of electronic device. Such an electronic system includes various types of computer readable media and interfaces for various other types of computer readable media. Electronic system 600 includes a main system bus 605, a central processing unit (CPU) 610, a system memory 615, a read-only memory (ROM) 620, a permanent storage device 625, input/output (I/O) interface 630, graphics processing unit(s) (GPUs) 635 that connect to the main system bus 605 through a PCIe bus connecting through the I/O interface 630, and a network 640. Additionally, a machine learning model and software-implemented AI/deep learning algorithm 645 (hereinafter referred to as the "deep learning processing unit and ML model 645") is installed on the electronic system 600. While the deep learning processing unit and ML model 645 may be stored in the permanent storage device 625, it is shown as a separate component here for exemplary purposes. Also, in some embodiments, the deep learning processing unit and ML model 645 are encapsulated in physically external hardware, but communicably connected, to the electronic system 600. For instance, a hardware-accelerated device configured to perform AI, deep learning, and machine learning algorithms with machine learning models, such as the hardware-accelerated deep learning processing unit 545 and machine learning models 555 described above, by reference to FIG. 5. A more detailed example of a hardware-accelerated deep learning processing unit is described further below, by reference to FIG. 7.

The main system bus 605 collectively represents all system, peripheral, and chipset buses that communicatively connect the numerous internal devices of the electronic system 600, accept for a PCIe bus connected in support of GPUs 635. Besides the GPUs 635, the main system bus 605 communicatively connects the CPU 610 with the ROM 620, the system memory 615, and the permanent storage device 625.

From these various memory units, the CPU 610 retrieves instructions to execute and data to process in order to execute the processes of the invention. For instance, collecting user pain and food inputs received through the network 640. The CPU 610 may be a single processor or a multi-core processor in different embodiments.

The read-only-memory (ROM) 620 stores static data and instructions that are needed by the CPU 610 and other modules of the electronic system. The permanent storage device 625, on the other hand, is a read-and-write memory device. The permanent storage device 625 is a non-volatile memory unit that stores instructions and data even when the electronic system 600 is off. Some embodiments of the invention use a mass-storage device (such as a magnetic or optical disk and its corresponding disk drive) as the permanent storage device 625.

Other embodiments use a removable storage device (such as a floppy disk or a flash drive) as the permanent storage device 625. Like the permanent storage device 625, the system memory 615 is a read-and-write memory device. However, unlike storage device 625, the system memory 615 is a volatile read-and-write memory, such as a random access memory. The system memory 615 stores some of the instructions and image data that the CPU 610 needs at runtime. In some embodiments, the software implemented code for the processes, described above by reference to FIGS. 1-4, are stored in the system memory 615, the permanent storage device 625, and/or the ROM 620. For example, the various memory units include instructions for processing food and pain inputs, categorizing food inputs in taxonomical categories, and identifying probably food and pain triggers in accordance with some embodiments. From these various memory units, the CPU 610 retrieves instructions to execute, transmits instructions and the user-provided food and pain data to the GPUs 635 for machine learning-based, massively parallel processing in some embodiments.

The main system bus 605 also connects to the input/output interface 630, which itself may connect to one or more external devices including, for example, alphanumeric keyboards and pointing devices (also called "cursor control devices"). Furthermore, other output devices may connect to the electronic system 600 via the I/O interface 630 including devices configured to display the 3D body model (or 2D body model) and reports, notifications, etc., in textual format. Examples of such other output devices include printers and display devices, such as liquid crystal displays (LCD) and organic light emitting diode (OLED) displays. Some embodiments include devices such as a touchscreen that functions as both input and output devices.

Finally, as shown in FIG. 6, bus 605 also couples electronic system 600 to a network 640 through a network adapter (not shown). In this manner, the computer can be a part of a network of computers (such as a local area network ("LAN"), a wide area network ("WAN"), or an intranet), or a network of networks (such as the Internet). Any or all components of electronic system 600 may be used in conjunction with the invention.

These functions described above can be implemented in digital electronic circuitry, in computer software, firmware or hardware. The techniques can be implemented using one or more computer program products. Programmable processors and computers can be packaged or included in other computing device forms, such as single board computers or mobile devices. The processes may be performed by one or more programmable processors and by one or more set of programmable logic circuitry. General and special purpose computing and storage devices can be interconnected through communication networks.

Some embodiments include electronic components, such as microprocessors, storage and memory that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media may store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

Figure 7:
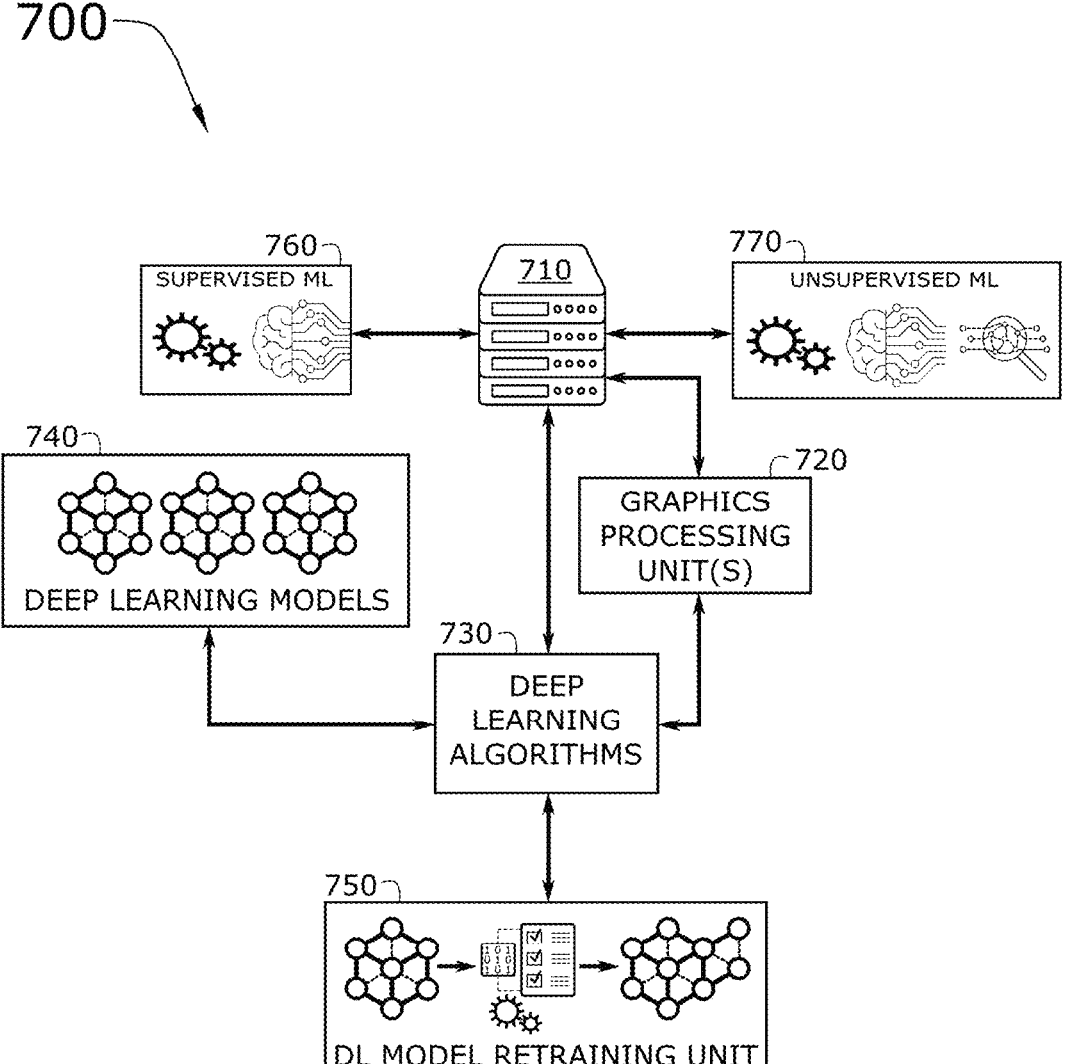
FIG. 7 conceptually illustrates a hardware-accelerated deep learning processing system utilized by the machine-learning based, interactive chronic pain and food trigger tracking system in some embodiments.

By way of example, FIG. 7 conceptually illustrates a hardware-accelerated deep learning processing system 700. The hardware-accelerated deep learning processing system 700 may be deployed as a hardware-based component of the machine-learning based, interactive chronic pain and food trigger tracking system. As shown in this figure, the hardware-accelerated deep learning processing system 700 comprises a deep learning processing server unit 710, graphics processing units (GPUs) 720, deep learning algorithms 730, deep learning models 740, and a deep learning model retraining unit 750.

In some embodiments, the deep learning processing server unit 710 provides access to machine learning aspects of the machine-learning based, interactive chronic pain and food trigger tracking system. In some embodiments, one or more of the deep learning algorithms 730, the deep learning models 740, and the deep learning model retraining unit are software-implemented components embedded in the deep learning server unit 710. In some other embodiments, one or more of the deep learning algorithms 730, one or more of the deep learning models 740, and the deep learning model retraining unit are externally connected to the deep learning server unit 710. In some embodiments, the deep learning algorithms 730 automatically determine the taxonomical categories of user-provided food input and are utilized to predict pain based on food intake reported by a user. The taxonomical categories and pain model inputs are stored for each particular user over time and are used to run the machine learning models on them to give the user feedback on possible food triggers for their chronic pain. For instance, the machine-learning based, interactive chronic pain and food trigger tracking system captures pain symptoms of the user and the deep learning algorithms 730 utilize a deep learning model 740 to predict pain symptoms based on the food input and the corresponding taxonomical categories of the food input. In some embodiments, external connection is a network connection over the Internet to an external deep learning service which the deep learning processing server unit 710 utilizes to predict pain triggering food items given a particular user's food intake, pain input, time, and history of both food and pain symptoms of the particular user.

In some embodiments, the GPUs 720 enable massively parallel processing by the deep learning processing server unit 710. The GPUs 720 may be incorporated into the deep learning processing server unit 710 (embedded) or separate from the deep learning processing server unit 710 as separate physical device hardware which is communicably connected to the deep learning processing server unit 710.

In some embodiments, the deep learning processing server unit 710 is configured to perform supervised machine learning 760 (or semi-supervised), such as when there is not a sufficiently large data pool from users providing food and pain input. The supervised learning (or semi-supervised learning) of the model could be reinforced by user feedback. In some embodiments, the deep learning processing server unit 710 is configured to perform unsupervised machine learning 770 after a sufficient user base is established and a sufficiently large data pool is available to train the model. Furthermore, the deep learning model retraining unit 750 would continuously retrain each of the deep learning models 740 utilized by the machine-learning based, interactive chronic pain and food trigger tracking system, and could be configured to train based on supervised learning, semi-supervised learning, reinforcement learning, or unsupervised learning. In this way, the machine-learning based, interactive chronic pain and food trigger tracking system is able to continually fine-tune the deep learning models 740 as more and more users register on the platform. With a large enough pool of registered users, a more generic unsupervised machine learning model could be used that gives users feedback even earlier on in the process. Notably, whether the deep learning models 740 are trained, retrained, and otherwise learn by supervised, semi-supervised, or supervised learning, the pain and food intake data provided by users, and pain prediction data output by the deep learning algorithms for those users, is encrypted to ensure strict user privacy over each user's personal health data.

While the invention has been described with reference to numerous specific details, one of ordinary skill in the art will recognize that the invention can be embodied in other specific forms without departing from the spirit of the invention. For instance, FIGS. 1-4 conceptually illustrate methods or processes. The specific operations of these methods/processes may not be performed in the exact order shown and described. Specific operations may not be performed in one continuous series of operations, and different specific operations may be performed in different embodiments. Furthermore, each method/process could be implemented using several sub-processes, or as part of a larger macro process. Thus, one of ordinary skill in the art would understand that the invention is not to be limited by the foregoing illustrative details, but rather is to be defined by the appended claims.

I claim:

1. A computer-implemented method for managing and determining chronic pain triggers:

providing a user with a visual touch screen 2D/3D body model enabled for interaction with the user and prompting a user to input a first bodily location on the 2D/3D body model of a first pain experienced by the user;

receiving, by a chronic pain and food trigger tracking app, structured data representing food or supplement intake during a first intake time period and pain symptom data corresponding to at least one symptom reporting time point, wherein the intake time period and the symptom reporting time are not required to occur simultaneously;

receiving, by the app, user input of a first pain experienced by the user at a first particular time that is one of (i) during the first period of time and (ii) after the first period of time elapses, wherein the user input of the first pain comprise a first bodily location of the first pain experienced by the user, a first type of pain that characterizes the first pain experienced by the user, and a first intensity of the first pain experienced by the user;

processing the intake data by mapping ingredients to one or more food classification using classification mapping database representing an ingredient hierarchy and collecting composite food records for meals within a prior temporal window;

generating feature vectors for correlation analysis by computing, for each classification, one or more statistical features derived from occurrence, exposure, or frequency with the window;

transmitting, to the front-end server by the app, the user input of the food intake information over the first period of time and the user input of the first pain experienced by the user at the first particular time, the composite food records, and intake data;

transmitting the user input of the food intake information over the first period of time and the user input of the first pain experienced by the user at the first particular time, by the front-end server, to a backend chronic pain and food trigger tracking server, food intake information over the first period of time and the user input of the first pain experienced by the user at the first particular time, the composite food records, and intake data;

training, by a deep learning processing unit that is communicably connected to the backend chronic pain and food trigger tracking server, an initial machine learning model for the user based on the food intake information over the first period of time and the user input of the first pain at the first particular time;

receiving, by the app operated by the user subsequent user input of additional food intake information over a second period of time after the first period of time elapses;

receiving, by the app, subsequent user input of a second pain experienced by the user at a second particular time that is one of (i) during the second period of time and (ii) after the second period of time;

wherein the subsequent user input of the second pain comprises a second bodily location of the second pain experienced by the user, a second type of pain that characterizes the second pain experienced by the user, and a second intensity of the second pain experienced by the user;

transmitting, to the front-end server by the chronic pain and food trigger tracking app, the subsequent user input of the additional food intake information over the second period of time and the subsequent user input of the second pain experienced by the user at the second particular time;

transmitting the subsequent user input of the additional food intake information over the second period of time and the subsequent user input of the second pain experienced by the user at the second particular time, by the front-end server, to the backend chronic pain and food trigger tracking server;

retraining, by the deep learning processing unit, the initial machine learning model for the user based on the additional food intake information over the second period of time and the subsequent user input of the second pain at the second period of time;

identifying, by the backend chronic pain and food trigger tracking server, a pain delta that expresses a change in pain for the user between the first pain at the first period of time and the second pain at the second period of time;

identifying, by the backend chronic pain and food trigger tracking server, correlations between food and pain for the user based on correlating the food intake and additional food intake information to the pain delta; and generating, by the backend server and based on the correlation between the pain delta and the food intake information and the additional food intake information, a trigger classification for a food that triggered a particular pain comprising one of the first pain and the second pain;

displaying, based on the trigger classification for a food that triggered a particular pain comprising one of the first pain and the second pain:

(i) structured dietary or supplement-use plan that removes or substitutes predicted trigger items above a confidence threshold, and/or (ii) real-time alerts advising the user to avoid the predicted trigger items.

2. The method of claim 1, further comprising comparing the structured intake data to a composite database that stores aggregated nutritional information and ingredient taxonomy.

3. The method of claim 1, wherein receiving intake data comprises text input, images processed by optical character recognition through a user interface, and optionally includes automated retrieval of food or supplement information from external databases and application programming interfaces.

4. The method of claim 1, wherein receiving intake data further comprises capturing an image of a food or supplement item with a device camera and processing the image using pattern recognition or machine learning techniques to identify components of the item.

5. The method of claim 1, wherein the structured intake data comprises food and supplement information annotated with tags for use in correlation analysis.

6. The chronic pain and food trigger tracking process method of claim 1 further comprising suggesting one or more therapeutic or behavioral skills, including Dialectical Behavior Therapy (DBT) skills for the user to practice over time based on the first pain and the second pain in response to predicted dietary or supplement triggers.

7. The method of claim 1, wherein predicting the likelihood of a trigger comprises generating a probability percentage for each predicted trigger and estimating a time interval between intake and symptom onset to inform intervention timing.

8. The method of claim 7, wherein predicting the trigger classification for the food comprises:

determining a taxonomical category for the pain delta; and calculating a probability for a taxonomical category of a food, wherein the calculated probability for the taxonomical category of the food being a trigger for the particular pain is based on the identified correlations between food and pain for the user in comparison with the onset time of the particular pain in connection with the time of consumption of the food.

9. The method of claim 1, wherein model selection further comprises, based on data availability:

(i) in an initial phase using user specific intake and pain data, applying at least one of a k-nearest-neighbor classifier and a single user regression analysis to predict trigger classifications;

(ii) after intake and pain data from a plurality of users is available, applying a model trained using the multiuser dataset and retrained by the deep learning processing unit; and (iii) refining the selected model(s) over time using user feedback.

10. The chronic pain and food trigger tracking process of claim 1 further comprising retrieving man-made food information for a man-made food item identified for a food in the food intake information and the additional food intake information.

11. The method of claim 1, wherein the personalized guidance includes displaying a confidence indicator for each predicted trigger and generating a user interface with reports, notifications, and probabilities of these triggers.

12. The method of claim 1, further comprising retraining the machine learning model based on user input or outcome-based metrics, including changes in pain severity after following personalized guidance.

13. The method of claim 1, wherein the machine learning model applies window-based temporal analysis to intake and symptom data based on time intervals between intake and symptom onset.

14. The method of claim 1, wherein encrypted user-level data or model outputs are aggregated without exposing raw user-level data.

15. The method of claim 1, wherein at least a portion of the model training or inference is performed on a user device prior to communication with the backend chronic pain and food trigger tracking server.

16. The method of claim 1, further comprising receiving user input of mental health information over time, and suggesting one or more therapeutic skills based on an analysis of the mental health information in combination with the pain delta and the food or supplement intake information.

17. The method of claim 1, wherein the correlations identified further comprise whether a supplement is helping, hurting, or having no effect on the user's chronic pain.

* * * * *